US010760119B2

(12) United States Patent
Yoon et al.

(10) Patent No.: US 10,760,119 B2
(45) Date of Patent: Sep. 1, 2020

(54) INTERFACIAL EFFECTS ENABLE DROPLET ACTUATION, INHIBITION RELIEF, AND EARLY SENSING OF POLYMERASE CHAIN REACTION

(71) Applicant: Arizona Board of Regents on Behalf of the University of Arizona, Tucson, AZ (US)

(72) Inventors: Jeong-Yeol Yoon, Tucson, AZ (US); Dustin Harshman, San Diego, CA (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 420 days.

(21) Appl. No.: 15/517,028

(22) PCT Filed: Oct. 23, 2015

(86) PCT No.: PCT/US2015/057081
§ 371 (c)(1),
(2) Date: Apr. 5, 2017

(87) PCT Pub. No.: WO2016/065240
PCT Pub. Date: Apr. 28, 2016

(65) Prior Publication Data
US 2017/0298416 A1    Oct. 19, 2017

Related U.S. Application Data

(60) Provisional application No. 62/068,468, filed on Oct. 24, 2014.

(51) Int. Cl.
*C12Q 1/68* (2018.01)
*B01L 3/00* (2006.01)
*B01L 7/00* (2006.01)
*C12Q 1/686* (2018.01)

(52) U.S. Cl.
CPC ........ *C12Q 1/686* (2013.01); *B01L 3/502784* (2013.01); *B01L 7/525* (2013.01); *B01L 7/54* (2013.01); *B01L 2200/0673* (2013.01); *B01L 2300/0861* (2013.01); *B01L 2300/185* (2013.01); *B01L 2400/0475* (2013.01); *B01L 2400/0487* (2013.01)

(58) Field of Classification Search
CPC combination set(s) only.
See application file for complete search history.

(56) References Cited

U.S. PATENT DOCUMENTS

| 4,767,468 A | 8/1988 | Finney |
| 8,541,176 B2 | 9/2013 | Pamula et al. |
| 2011/0159547 A1 | 6/2011 | Yu et al. |

(Continued)

OTHER PUBLICATIONS

Harshman et al., "Rapid Molecular Diagnosis of Infective Endocarditis: Developing Dots qPCR," Poster presented at MicroTAS 2014, San Antonio, Texas, Oct. 26, 2014.

(Continued)

*Primary Examiner* — Brian R Gordon
(74) *Attorney, Agent, or Firm* — Klarquist Sparkman, LLP

(57) ABSTRACT

Disclosed are devices, systems and methods of use utilizing interfacial effects enabling droplet actuation, inhibition and early sensing of molecular reactions, such as of polymerase chain reaction.

8 Claims, 10 Drawing Sheets

Specification includes a Sequence Listing.

(56) References Cited

U.S. PATENT DOCUMENTS

| | | |
|---|---|---|
| 2011/0268151 A1 | 11/2011 | Hadwen et al. |
| 2013/0149710 A1 | 6/2013 | Yoon et al. |
| 2013/0183717 A1 | 7/2013 | Marble et al. |
| 2013/0288254 A1* | 10/2013 | Pollack ............ B01L 3/502792 435/6.12 |

OTHER PUBLICATIONS

Harshman et al., "Innovative qPCR using interfacial effects to enable low threshold cycle detection and inhibition relief," *Sci Adv.* 1:E1400061, 2015.

* cited by examiner

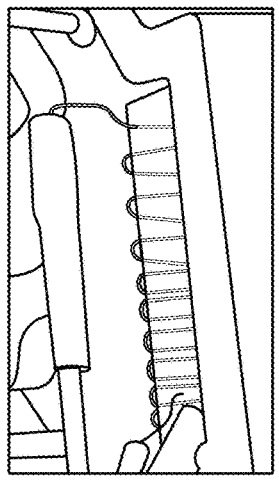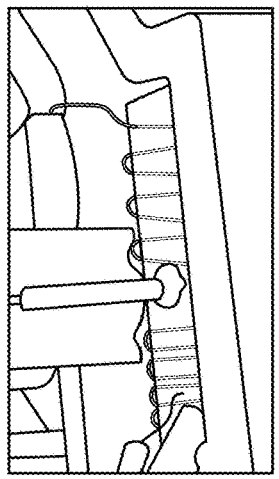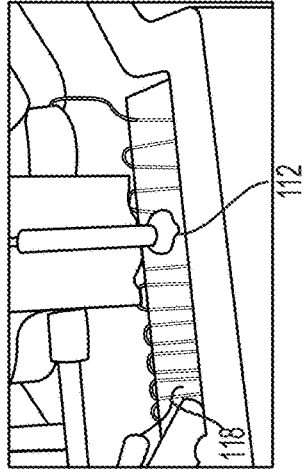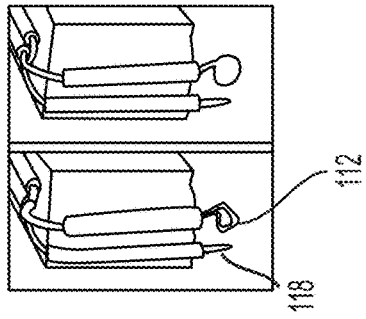

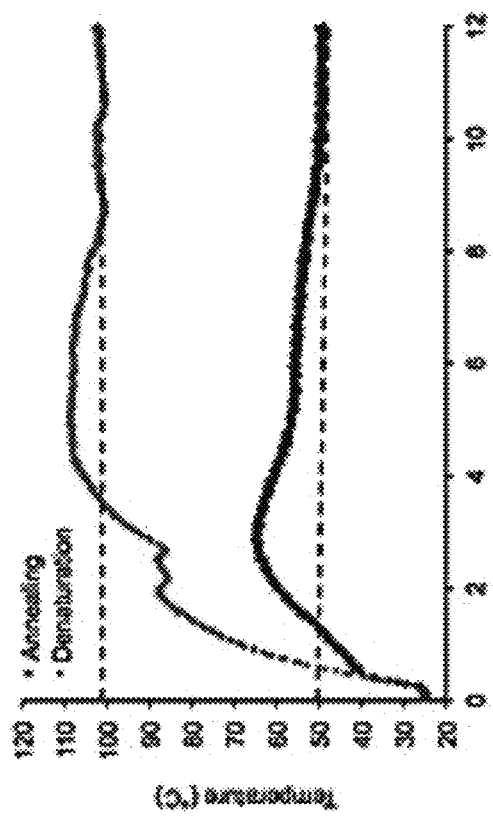
FIG. 2A
FIG. 2B
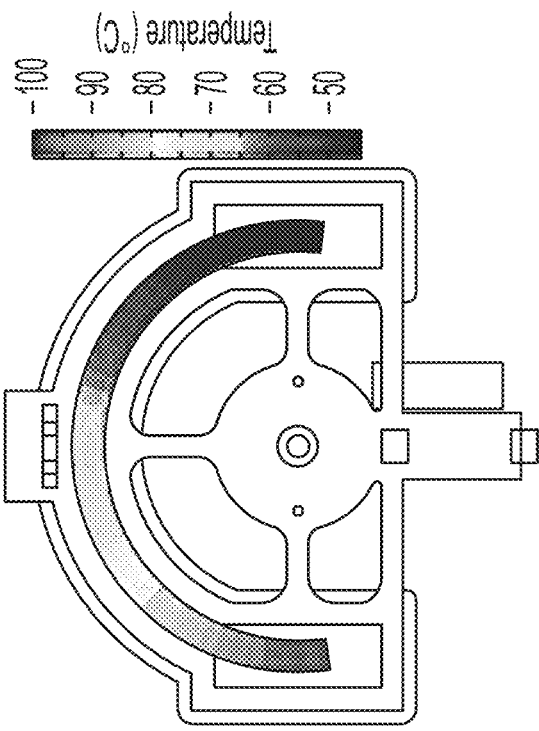
FIG. 2C
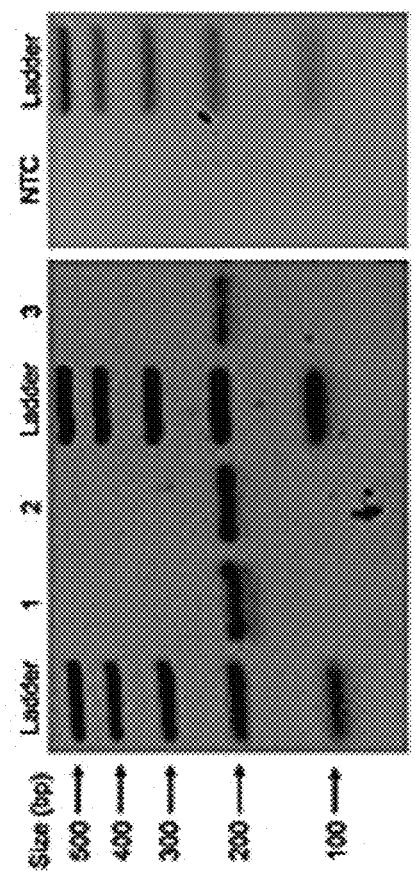
FIG. 2D
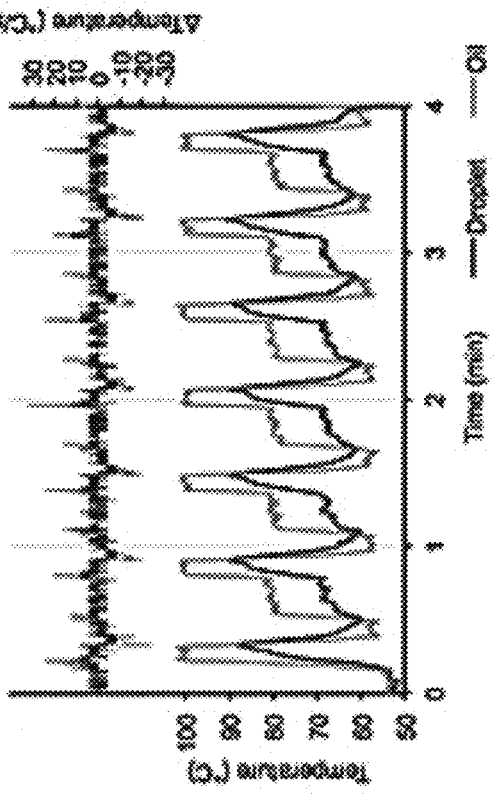

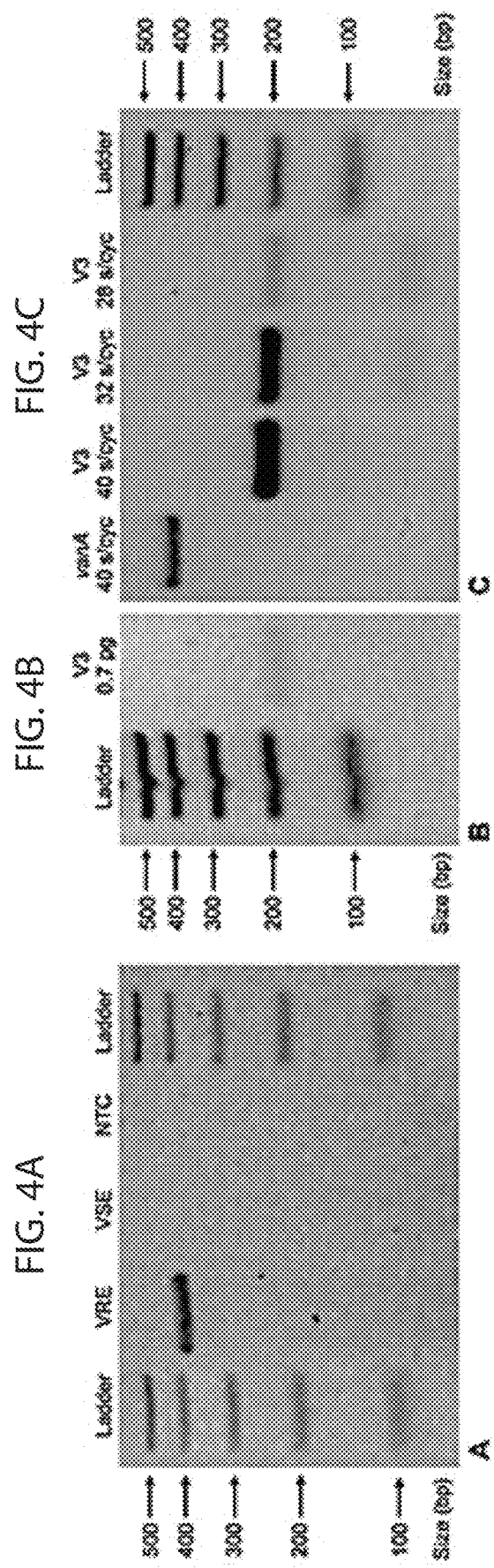

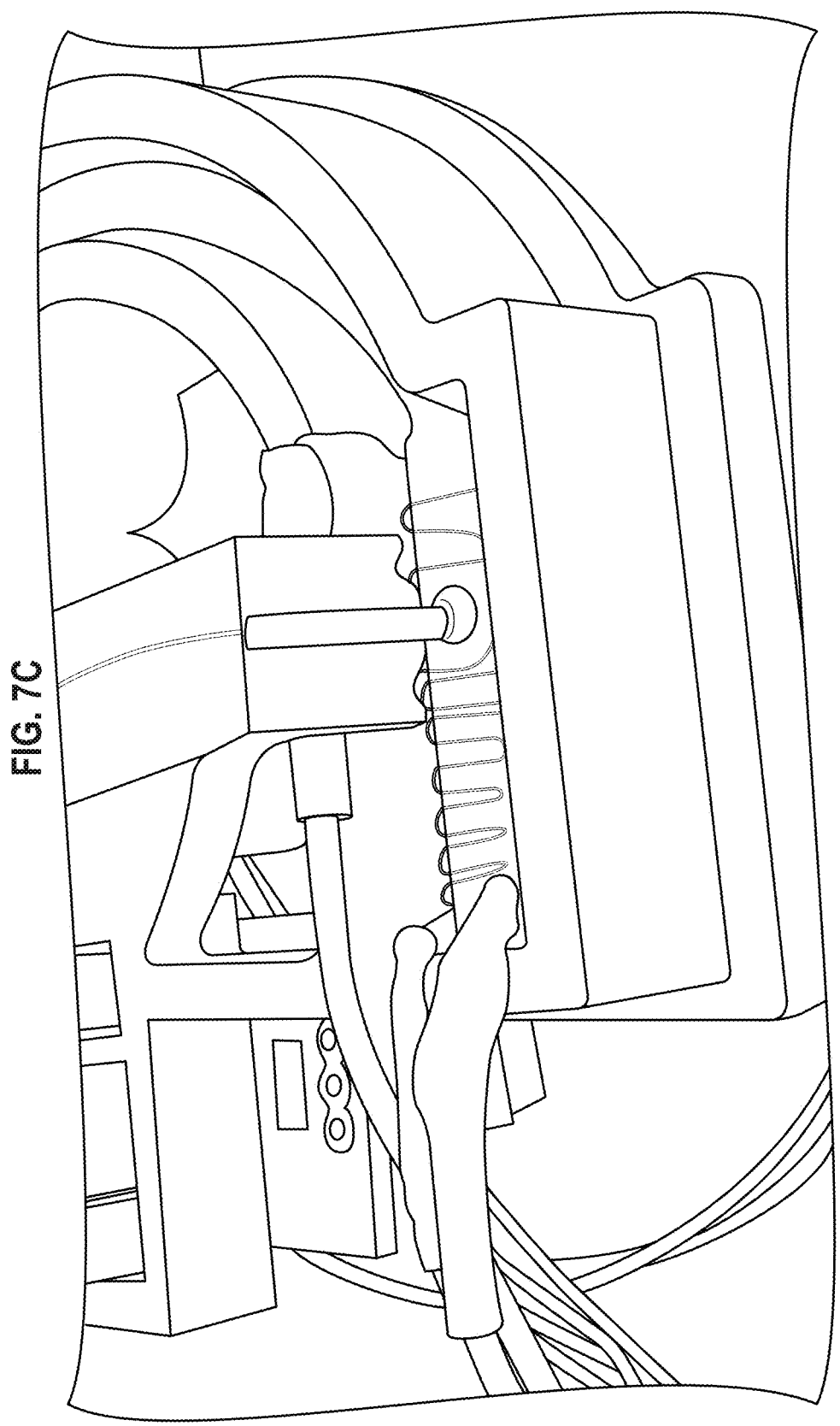

INTERFACIAL EFFECTS ENABLE DROPLET ACTUATION, INHIBITION RELIEF, AND EARLY SENSING OF POLYMERASE CHAIN REACTION

CROSS REFERENCE TO RELATED APPLICATION

This application is the § 371 U.S. National Stage of International Application No. PCT/US2015/057081, filed Oct. 23, 2015, which was published in English under PCT Article 21(2), which in turn claims the benefit of U.S. Provisional Application No. 62/068,468, filed Oct. 24, 2014, which is hereby incorporated herein by reference its entirety.

ACKNOWLEDGMENT OF GOVERNMENT SUPPORT

This invention was made with government support under Grant No. T32 HL007955 awarded by the National Institutes of Health and Grant No. 1511093 award by the National Science Foundation. The government has certain rights in the invention.

FIELD

This disclosure relates to devices, systems and methods of use utilizing interfacial effects for droplet actuation, inhibition relief and early sensing of molecular reactions, such as of polymerase chain reaction.

BACKGROUND

The ability to sense molecular reactions, such as polymerase chain reaction (PCR), with precision and efficiency is needed. Currently available systems often do not allow for quantification of DNA in a time efficient, convenient manner. For example, there is an urgent need for innovative detection technologies to detect and monitor various conditions, including antibiotic resistance. Blood and tissue culture and current molecular technologies remain too slow to obviate the need for empiric therapy. Thus, a continuing need exists for improved systems and methods that allow for rapid, efficient detection of DNA which can be useful in many areas, including for rapid diagnosis and timely, accurate treatments.

SUMMARY

Disclosed herein is droplet on thermocouple silhouette real-time polymerase chain reaction (DOTS qPCR) which utilizes interfacial effects for droplet actuation, inhibition relief and sensing. The reaction droplet is stabilized by interfacial tension as a motor positions it in an oil heat gradient chamber by temperature feedback. Only minimal sample preparation (tissue grinding and liquid phase pipetting) is necessary due to inhibition relief by protein compartmentalization at the oil-water interface. Thus, the disclosed device is a field-deployable, handheld PCR apparatus with reduced thermocycling time which utilizes interfacial effects to detect and quantify DNA.

In some examples, the disclosed device utilizes interfacial effects to detect antibiotic resistance, such as in the differentiation of vancomycin-resistant *Enterococcus* and vancomycin-sensitive *Enterococcus* is demonstrated by amplification of the vanA gene. Thermocycling speeds up to 28 s/cycle in the presence of tissue contaminants are achieved by oil/droplet temperature offsets as demonstrated by amplification of 16s rRNA gene hypervariable region V3 from inoculated heart valve tissue. Sub-picogram limit of detection is shown by amplification of the 16s rRNA V3 region from 0.7 pg purified gDNA. Langmuir and Gibbs adsorption isotherms are used to describe interfacial tension decrease upon amplification, and a log-linear relationship is presented for real-time quantification at the fifth thermocycle, by imaging the droplet silhouette with a smartphone. Commercially available real-time PCR systems that rely on fluorescent detection have substantially higher threshold cycles and require expensive optical components and extensive sample preparation. For example, conventionally thermocycled PCR cocktails containing $1.5 \times 10^4$ genomic equivalents have a 20.74% interfacial tension decrease at the tenth thermocycle with saturation thereafter. This dramatic reduction in interfacial tension, during early thermocycles, upon the exponential increase in bulk dsDNA/SYBR complex causes droplet volume loss, as 1-2 μm droplets become emulsified in the oil phase. The droplet volume decrease scales linearly with the logarithm of initial target amount and is used for quantification at the fifth thermocycle by DOTS qPCR. The fifth thermocycle is reached in 4 minutes and tissue grinding and pipetting takes 1 minute, meaning total time from sample-to-answer is 5 min. The speed of DOTS qPCR enables its use at the point-of-care for initial therapy prescription.

In one embodiment, a disclosed apparatus includes at least one chamber, such as two chambers containing a hydrophobic liquid, wherein a first chamber of the two chambers maintains the hydrophobic liquid at a temperature at or above the maximum temperature for a respective stage in thermocycling, and a second of the two chambers maintains the hydrophobic liquid at a temperature at or below the minimum temperature for a respective stage in thermocycling; a channel for hydraulically connecting the two chambers and containing the hydrophobic liquid; a movement device adapted to move between the two chambers and along the channel; a droplet manipulating device coupled to the movement device and immersed in the hydrophobic liquid, wherein the droplet manipulating device comprises a temperature sensing device configured to sense a temperature inside a droplet placed within the droplet manipulating device; and a controller operably connected to the movement device and the temperature sensing device within the droplet manipulating device, the controller being configured to command the movement device along the channel based on the sensed temperature inside the droplet. In some examples, the disclosed apparatus includes a multi-chamber array.

In some embodiments, a disclosed device includes a chamber containing a hydrophobic liquid configured to maintain the hydrophobic liquid at a temperature at or above the maximum temperature for a respective stage in thermocycling; a channel hydraulically coupled to the chamber and extending from the chamber a distance sufficient to form a temperature gradient along the hydrophobic liquid; a movement device adapted to move along the channel; a droplet manipulating device coupled to the movement device and immersed in the hydrophobic liquid, wherein the droplet manipulating device comprises a temperature sensing device configured to sense a temperature inside a droplet placed within the droplet manipulating device; and a controller operably connected to the movement device and the temperature sensing device, the controller being configured to command the movement device along the channel based on the sensed temperature inside the droplet.

Also disclosed are methods of using the disclosed devices, such as for methods of controlling PCR amplification. In one embodiment, a method of controlling PCR amplification, the method includes dispensing a droplet containing a PCR cocktail into a thermocouple silhouette, wherein the thermocouple is configured to sense a temperature internal to the droplet; measuring an initial diameter of the droplet; thermocycling the droplet based on the temperature internal to the droplet; measuring a current diameter of the droplet between thermocycling cycles; and stopping the thermocyclying responsive to a preset decrease in the current diameter of the droplet compared to the initial diameter of the droplet. In some embodiments, a method of amplifying a nucleic acid is disclosed. In one example, this method includes dispensing a droplet into a thermocouple loop, wherein the thermocouple loop is immersed in a hydrophobic liquid with a temperature gradient; sensing a temperature inside the droplet; and moving the droplet along the temperature gradient according to a predetermined temperature profile for the droplet.

The foregoing and other features and advantages of the disclosure will become more apparent from the following detailed description, which proceeds with reference to the accompanying figures.

BRIEF DESCRIPTION OF THE DRAWINGS

FIGS. 1A-1F are digital images of an exemplary droplet on thermocouple silhouette real-time PCR (DOTS qPCR) device 100. FIG. 1A illustrates the various components of a disclosed DOTS qPCR device 100 including: a heat gradient chamber with PID controlled heaters at 180 degrees, feedback thermocouples mounted 5 mm above surface of heaters, motor arm with looped thermocouple mounted for droplet suspension in heated oil and reaction temperature monitoring and positioning feedback, viewing window at center of gradient chamber, and lens tube to focus and magnify the droplet image onto the smartphone camera. In some embodiments, all components are disposable after one use except for the motor, lens tube, and smartphone.

FIG. 1B provides an alternate view of the heat gradient chamber of an exemplary DOTS qPCR device 100 showing reaction droplet on looped thermocouple moving to the low temperature side of the gradient for the annealing phase of the reaction.

FIG. 1C shows two exemplary thermocouples mounted on a motor arm. The straight thermocouple is used for oil temperature measurement, and the looped thermocouple holds the droplet and measures the droplet temperature.

FIGS. 1D and 1E are still images of a submerged droplet moving back and forth continuously at the low-temperature region. The thermocouple junction is inside the droplet to monitor the reaction temperature. Droplet temperature feedback is used by the motor program to accurately position the droplet in the heat gradient.

FIG. 1F is a still image of the droplet moving away from the low-temperature region after completing annealing, to be positioned at a warmer region corresponding to the optimum temperature for Taq polymerase extension of the PCR amplicon.

FIG. 2A is a temperature color map of the heat gradient established between heaters from a maximum of 100° C. at the left and minimum of 45° C. at the right. Measured by a thermocouple mounted on the motor arm, traveling at 17.6/s around the chamber arc.

FIG. 2B is a heat ramp of the two extreme temperature regions from 25° C. to equilibrium at temperature setpoints within 10 minutes.

FIG. 2C is a representative thermocycling profile of internal droplet temperature and surrounding oil temperature, indicating reproducibility of temperatures over many cycles even at sub-minute cycle times. The temperatures at each phase were 90.4±0.2° C. for denaturation, 68.4-0.2° C. for extension, and 60.2±0.2° C. for annealing. Droplet ramp rates up to 12° C./s and oil ramp rates up to 32° C./s were achieved by moving the droplet within the heat gradient.

FIG. 2D is a digital image of a gel electropherogram showing the results from three successive trials (lanes 1-3) to amplify the 196 bp 16S rRNA V3 amplicon from 7 pg purified $K.$ $pneumoniae$ genomic DNA (equivalent to 1.4× $10^3$ genomic copies) and a no template control (NTC) sample. The thermocycling speed was 48 s/cycle, and 30 cycles were conducted. The band intensities in lanes 1-3 have a coefficient of variation of 4.0%.

FIG. 4A is a digital image of a gel electropherogram showing the differentiation of vancomycin-resistant $Enterococcus$ (VRE) and vancomycin-sensitive $Enterococcus$ (VSE) by multiplexed amplification of the 377-bp vanA amplicon directly from bacterial culture. Simultaneous thermocycling was achieved by mounting three droplets on different thermocouples on the same motor arm. Lane 1: 1-kb plus DNA ladder; lane 2: VRE; lane 3: VSE; lane 4: no template control (NTC); and lane 5: 1-kb plus DNA ladder.

FIG. 4B is a digital image of a gel electropherogram showing the limit of detection at the sub-picogram level by amplification of the 196 bp 16S rRNA V3 amplicon from 0.7 pg $K.$ $pneumoniae$ genomic DNA (equivalent to 1.4×$10^2$ genomic copies) at the speed of 48 s/cycle. Lane 1: 1-kb plus DNA ladder; and lane 2: 0.7 pg gDNA.

FIG. 4C is a digital image of a gel electropherogram showing rapid amplification of the 16s rRNA V3 amplicon and vanA amplicon in the presence of tissue contaminants in 30 cycles. Lane 1: vanA amplified at 40 s/cycle (20 min) from $7 \times 10^5$ CFU VRE inoculated to valve tissue; V3 amplified from $7 \times 10^5$ CFU VRE inoculated to valve tissue, lane 2: at 40 s/cycle (20 min); lane 3: at 32 s/cycle (16 min); lane 4: at 28 s/cycle (14 min); and lane 5: 1-kb plus DNA ladder.

FIG. 6A is a graph of the results from quantitating band intensities at the 196 bp region of the gel images were quantified, normalized to the intensity at $C_0$, and plotted against $C_n$. The product band is first detected at $C_{20}$, and no product band is detected for the NTC.

FIG. 6B is a fluorescence qPCR amplification curve for the 16S rRNA V3 amplicon (196 bp) amplified from 75 pg K. pneumoniae genomic DNA ($1.5 \times 10^4$ genomic copies) and NTC. The $C_t$ value is 21.11±0.06.

FIG. 6C is a graph providing the interfacial tensions of the PCRs analyzed with an FTÅ (First Ten Ås) 200 contact angle and interfacial tension analyzer. The percent change in interfacial tension, $d\gamma/\gamma_0=(\gamma_0-\gamma_n)/\gamma_0$, is plotted against $C_n$. The γ of the reaction with DNA and SG decreases by 21% by $C_{10}$ and remains the same thereafter. The γ of the reaction with DNA but without SG increases by 11% by $C_5$ and then further increases to 19% by $C_{30}$. The γ of the SG NTC reaction increases by 6% by $C_5$ and fluctuates within 4% thereafter.

FIG. 7C is a digital image of a DOTS qPCR in operation. The motor arm with mounted thermocouple loop submerged beneath the surface of the oil is positioned at the low temperature region of the heat gradient chamber. A 5-10 μL droplet of PCR cocktail is positioned on the thermocouple loop by pipette, and the thermocycling program is initiated. Prior to the first thermocycle, the droplet is positioned in front of the viewing window and an image of the droplet silhouette at cycle zero is captured by smartphone camera. The droplet then moves to the high temperature region for the initial denaturation. Once the desired droplet temperature has been achieved, the droplet moves to the low temperature region for annealing, followed by extension at the 72° C. region. Thermocycling repeats in this fashion until the fifth thermocycle when another image of the droplet silhouette is taken for analysis and quantification of initial target concentration.

FIG. 8A is as DOTS qPCR standard curve for 16S amplification of the V3 amplicon from *Klebsiella pneumoniae* genomic DNA, in the range of $1.5 \times 10^2$ to $1.5 \times 10^5$ genomic copies. A trend line was fitted to the data by linear regression analysis: $\log(N_0)= -0.48C_t+6.6$; $R^2=0.981$. In DOTS qPCR, the $C_t$ values for NTC and $1.5 \times 10^2$, $1.5 \times 10^3$, $1.5 \times 10^4$, and $1.5 \times 10^5$ genomic copies were 14.4±0.4, 9.0±0.6, 7.5±0.4, 4.6±0.3, and 3.1±0.2, respectively.

FIG. 8B is a fluorescence qPCR standard curve for 16S amplification of the V3 amplicon from *Klebsiella pneumoniae* genomic DNA, in the same range. A trend line was fitted to the data by linear regression analysis: $\log(No)=-0.24C_t+9.4$; $R^2=0.996$. In fluorescence qPCR, the $C_t$ values for NTC and $1.5 \times 10^2$, $1.5 \times 10^3$, $1.5 \times 10^4$, and $1.5 \times 10^5$ genomic copies were 32.4±0.1, 29.88±0.03, 25.28±0.07, 21.11±0.06, and 17.66±0.04, respectively.

SEQUENCE LISTING

Figure 1B:
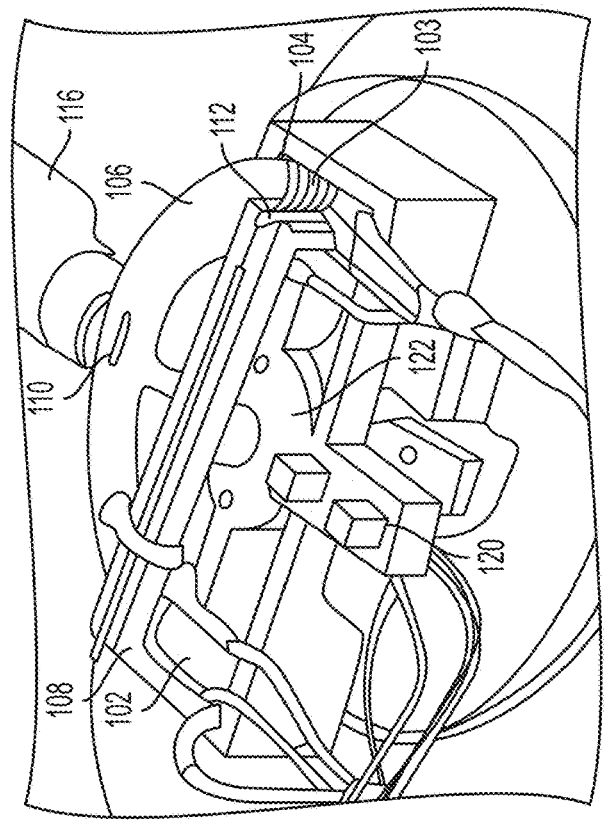

The instant application contains a Sequence Listing which has been submitted electronically in ASCII format and is hereby incorporated by reference in its entirety. Said ASCII copy, created on Mar. 31, 2017, is named 8085-93917-03_SL.txt and is 1.691 kilobytes in size.

The nucleic acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NOs: 1-6 are primer sequences.

DETAILED DESCRIPTION OF SEVERAL EMBODIMENTS

The disclosure is set forth below in the context of multiple representative embodiments, which are not intended to be limiting in any way.

The drawings are intended to illustrate the general manner of construction and are not necessarily to scale. In the detailed description and in the drawings themselves, specific illustrative examples are shown and described herein in detail. It will be understood, however, that the drawings and the detailed description are not intended to limit the invention to the particular forms disclosed, but are merely illustrative and intended to teach one of ordinary skill how to make and/or use the invention claimed herein.

The described things and methods described herein should not be construed as being limiting in any way. Instead, this disclosure is directed toward all novel and non-obvious features and aspects of the various disclosed embodiments, alone and in various combinations and sub-combinations with one another. The disclosed things and methods are not limited to any specific aspect or feature or combinations thereof, nor do the disclosed things and methods require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed things and methods can be used in conjunction with other things and method.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. In addition, all GenBank accession numbers are herein incorporated by reference as they appear in the database on Oct. 24, 2014. In case of conflict, the present specification, including explanations of terms, will control.

I. Introduction

Two years after the U.S. Food and Drug Administration (FDA) approval of methicillin, methicillin-resistant *Staphylococcus aureus* (MRSA) emerged, serving as a warning of rapid bacterial evolution in response to selective pressures. Vancomycin has become the standard of care and last resort for treating MRSA, but enterococci with vancomycin-resistance (VRE) have a 10.8-kb transposon, Tn1546 which contains the ligase-encoding gene, vanA. Tn1546 has transconjugated from enterococci to MRSA on twelve independent clinical occasions, resulting in vancomycin-resistant *Staphylococcus aureus* (VRSA). The rapid evolution of bacteria and the transfer of vancomycin-resistance genes undermine our ability to treat serious infections and indicate an urgent need for technological innovation to enable widespread surveillance of antibiotic resistance dissemination. The co-existence of VRE and MRSA in the clinic, especially in infective endocarditis (IE), results in difficult disease management and significant morbidity and mortality despite medical advancements. Traditional diagnosis of IE includes transesophegeal echocardiography, blood culture, and heart valve tissue culture. Rapid diagnosis and immediate directed therapy of IE are vital, leading to great interest in molecular approaches such as gene specific PCR and 16S hypervariable region PCR. These approaches have been proven to substantially improve diagnostic outcomes, but empiric antibiotic therapy must be initiated while test results are awaited, complicating disease management by diminishing protective flora and inducing resistance. To alleviate the need for empiric therapy, new technologies are being developed to decrease the time to diagnosis. The Roche LightCycler can detect 25 clinically important pathogens from whole blood within 6 hours, *S. aureus* genomic DNA can be quickly detected from whole blood with the Cepheid GeneXpert, and automated microscopy of immobilized bacterial cells growing in channels with varying antibiotic conditions can determine susceptibility phenotypes in 4 hours on the Accelerate ID/AST system.

Unfortunately, sample-to-answer information within the clinical decision making window to forego empiric therapy (less than 10 minutes) has yet to be realized. As participants in this high-speed race against bacterial evolution, disclosed herein is a droplet-based real-time PCR method that relies on interfacial effects for droplet actuation, protein compartmentalization and reaction sensing. Droplet actuation for conducting PCR has been previously achieved by electrowetting-on-dielectric (EWOD) using an interfacial tension gradient and by lab-on-a-chip using plug flow in microchannels. Similar techniques utilize a nanostructured surface to minimize surface fouling and enable repeated droplet actuations. While droplet fluidic phenomena have been extensively studied for droplet actuation in automated rapid assays, sensing modalities have been limited to fluorescence, colorimetry, surface plasmon resonance, and electrochemistry.

Here the inventors disclose the utility of droplet on thermocouple silhouette real-time PCR (DOTS qPCR) to achieve thermocycling times as fast as 28 s/cycle, prevention of evaporation by silicone oil immersion of the reaction droplet, droplet stabilization on the thermocouple by interfacial tension, compartmentalization of contaminating proteins at the oil-water interface without surface fouling, sub-picogram limit of detection, and real-time detection in 4 minutes by droplet on thermocouple silhouette (DOTS) analysis. This novel detection modality revolutionizes qPCR, which has been reliant on fluorescence detection for decades, by enabling detection as early as the fifth thermocycle. DOTS qPCR meets the speed requirement to forego empiric antibiotics by providing sample-to-answer times of 5 minutes, and its performance has been demonstrated using 16S rRNA gene hypervariable region and vanA gene amplification. DOTS qPCR is intelligibly designed to be readily adopted as a point-of-care diagnostic, epitomizing simplicity, small form factor, mobile integration and disposability.

Use of DOTS qPCR include providing clinicians with diagnostic information about tissue infections in the clinic or operating room at the exact time of initial antibiotic prescription, without extensive sample preparation or laboratory infrastructure.

II. Terms

As used in this application and in the claims, the singular forms "a," "an," and "the" include the plural forms unless the context clearly dictates otherwise. Additionally, the term "includes" means "comprises." Further, the term "coupled" encompasses mechanical as well as other practical ways of coupling or linking items together, and does not exclude the presence of intermediate elements between the coupled items.

The description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In the following description, certain terms may be used such as "up." "down,", "upper," "lower." "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

In order to facilitate review of the various embodiments of the disclosure, the following explanations of specific terms are provided:

Biological sample: A biological specimen containing genomic DNA. RNA (including mRNA and microRNA), protein, or combinations thereof, obtained from a subject. Examples include, but are not limited to, saliva, peripheral blood, urine, tissue biopsy, surgical specimen, and autopsy material. In one example, a sample includes a tissue biopsy, such as from a patient suspected of having or likely to have a particular condition/disease or a healthy control subject. In other embodiments, the biological sample is blood, or a component thereof, such as plasma or serum.

Control: A "control" refers to a sample or standard used for comparison with a test sample. In some embodiments, the control is a sample obtained from a healthy patient (or plurality of patients) (also referred to herein as a "normal" control). In some embodiments, the control is a historical control or standard value (i.e. a previously tested control sample or group of samples that represent baseline or normal values. In some examples the control is a standard value representing the average value (or average range of values) obtained from a plurality of patient samples from normal patients.

Diagnosis: The process of identifying a disease by its signs, symptoms and results of various tests. The conclusion reached through that process is also called "a diagnosis." Forms of diagnostic testing commonly performed include blood tests, medical imaging, genetic analysis, molecular marker analysis, urinalysis, biopsy and histology. Diagnostic methods differ in their sensitivity and specificity. The "sensitivity" of a diagnostic assay is the percentage of diseased individuals (for example, individuals with an infection) who test positive (percent of true positives). The "specificity" of a diagnostic assay is I minus the false positive rate, where the false positive rate is defined as the proportion of those without the disease who test positive. While a particular diagnostic method may not provide a definitive diagnosis of a condition, it is effective if the method provides a positive indication that aids in diagnosis. "Prognostic" is the probability of development (or for example, the probability of severity) of a pathologic condition.

Effective amount: An amount of agent that is sufficient to generate a desired response, such as reducing or inhibiting one or more signs or symptoms associated with a condition or disease. When administered to a subject, a dosage will generally be used that will achieve target tissue concentrations. In some examples, an "effective amount" is one that treats one or more symptoms and/or underlying causes of any of a disorder or disease.

Infectious disease: Any disease caused by an infectious agent. Examples of infectious pathogens include, but are not limited to: viruses, bacteria, *mycoplasma* and fungi. In a particular example, it is a disease caused by at least one type of infectious pathogen. In another example, it is a disease caused by at least two different types of infectious pathogens. Infectious diseases can affect any body system, be acute (short-acting) or chronic/persistent (long-acting), occur with or without fever, strike any age group, and overlap each other. Infectious diseases can be opportunistic infections, in that they occur more frequently in immunocompromised subjects Viral diseases commonly occur after immunosuppression due to re-activation of viruses already present in the recipient. Particular examples of viral infections include, but are not limited to, cytomegalovirus (CMV) pneumonia, enteritis and retinitis; Epstein-Barr virus (EBV) lymphoproliferative disease; chicken pox/shingles (caused by varicella zoster virus, VZV); HSV-1 and -2 mucositis; HSV-6 encephalitis. BK-virus hemorrhagic cystitis; viral influenza; pneumonia from respiratory syncytial virus (RSV); AIDS (caused by HIV); and hepatitis A, B or C. Opportunistic infections occur in a subject with a compromised immune system. These infections include, but are not limited to cytomegalovirus, *Candida albicans*, human immunodeficiency virus, *Staphylococcus aureus, Steptococcus pyogenes, Pseudomonas as aenruginosa, Acinteobacter baumanni, Toxoplasma gondii, Pneumocystitis carinii*, or *Aspergillus* infections.

Additional examples of infectious virus include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example. Hantaan viruses, bunga viruses, phleboviruses and Nairo viruses); Arena viridae (hemorrhagic fever viruses); Reoriridae (e.g., reoviruses, orbiviurses and rotaviruses); Birnaviridae: Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of fungal infections include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans.*

Examples of infectious bacteria include: *Helicobacter pyloris, Borelia burgdorferi, Legionella pneumophilia, Mycobacteria sps* (such as, *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcurrs pyogenes* (Group A *Streptococcus*), *Streptococcus agalactiae* (Group B *Streptococcus*). *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira*, and *Actinomyces israelli*. Other infectious organisms (such as protists) include: *Plasmodium falciparum* and *Toxoplasma gondii*.

Infective endocarditis (IE): An inflammation of the endocardium, most typically on the heart valves, caused by the growth of bacterial vegetation, in which both *S. aureus* and Enterococci are implicated. The devices, systems and methods disclosed herein can be used to detect and diagnose IE.

Patient or Subject: A term that includes human and non-human animals, such as those having an adrenocortical tumor. In one example, the patient or subject is a mammal, such as a human. "Patient" and "subject" are used interchangeably herein.

Polymerase Chain Reaction: The Polymerase Chain Reaction (PCR) is a method for detecting and amplifying DNA and RNA. PCR has unlimited sensitivity and unparalleled specificity. It is an essential tool and medical research and clinical medicine. It is used extensively for detecting infectious disease organisms and detecting gene mutations. Reverse transcription PCR (RT-PCR) is a variant of PCR in which an RNA strand is first reverse transcribed to complementary DNA (cDNA) using the enzyme reverse transcriptase. The cDNA is then amplified using traditional PCR.

PCR is an in vitro amplification technique that increases the number of copies of a nucleic acid molecule (for example, a nucleic acid molecule in a sample or specimen). In particular examples, amplification of a nucleic acid molecule of defined length is achieved by multiple cycles of a three-step procedure involving denaturing a DNA template, annealing oligonucleotide primer pairs to opposite strands of the template, and extending the primers with a thermally stable DNA polymerase to copy each strand of the template. Each step of a PCR cycle is carried out at a specific temperature. Target DNA is denatured at high temperature (such as at 95-98° C., such as about 95, 96, 97, or 98° C.). The temperature for annealing primers to complementary target DNA strands by nucleic acid hybridization is typically sequence-specific. Common primer-template annealing temperatures are between about 50-56° C., such as about 50, 51, 52, 53, 54, 55, or 56° C. Primer extension is carried out at a polymerase-specific temperature. Repeated polymerase exposure to high temperature in the denaturing step necessitates use of a thermal-stable polymerase, many of which are known in the art. In particular examples, the Taq DNA polymerase is used, and extension is carried out at about 72° C.

Exemplary embodiments of the devices and systems disclosed herein are used to amplify DNA by PCR. However, one of skill in the art will recognize that the described systems can be used in other exemplary methods of DNA amplification such as isothermal amplification methods, which can use fewer than three temperature-controlled chambers of the described PCR vessel. Representative and non-limiting examples of isothermal in vitro amplification techniques include strand-displacement amplification (see U.S. Pat. No. 5,744,311); transcription-free isothermal amplification (see U.S. Pat. No. 6,033,881); repair chain-reaction amplification (see WO 90/01069); ligase chain-reaction amplification (see EP-A-320 308); gap-filling ligase chain-reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

The product of a PCR or other amplification technique can be characterized by various standard techniques known in the art, such as electrophoresis, restriction endonuclease cleavage patterns, oligonucleotide hybridization or ligation, and/or nucleic acid sequencing.

PCR and other amplification methods and techniques for characterizing amplification products are well-known in the art, and are described, for example, in Ausubel et al. (eds.), *Current Protocols in Molecular Biology*, published by Wiley InterScience, 2011 (ISSN 1934-3639). Additionally, methods for preparing and using nucleic acid primers are described, for example, in Sambrook et al. (In *Molecular Cloning: A Laboratory Manual*, CSHL, New York, 1989), and Innis et al. (*PCR Protocols, A Guide to Methods and Applications*, Academic Press, Inc., San Diego, Calif., 1990).

In particular embodiments of PCR, known as real-time or quantitative PCR, methods and devices are used for detecting and measuring products generated during each PCR cycle, which are proportionate to the amount of template nucleic acid prior to the start of PCR. The information obtained, such as an amplification curve, can in some examples be used to quantify the initial amounts of template nucleic acid sequence. In particular embodiments, real-time PCR is accomplished using nucleic acid probes that can be included in an amplification reaction, for example to permit detection of formed amplicons (such as in real time). In one example, the detectable label associated with the probe is a fluorophore. The fluorescence signal intensity can be related to the amount of PCR product (amplicon) by a product-dependent decrease of the quench of a reporter fluorophore, or by an increase of the Förster resonance energy transfer (FRET) from a donor to an acceptor fluorophore. FRET is the radiationless transfer of excitation energy by dipole-dipole interaction between fluorophores with overlapping emission and excitation spectra. Because the FRET and the quench efficiency are strongly dependent on the distance between the fluorophores, the PCR-product-dependent change in the distance between the fluorophore can be used to generate the sequence-specific signals.

Several different probes can be used in real-time PCR methods. All can function by a decrease of quench or an increase of FRET. In one example, a cyanine dye probe is utilized, such as SYBR Green, SYBR Green II, SYBR Gold, Oxazole Yello, Thiazole Orange or PicoGreen. In other examples, 5' nuclease fluorogenic target-specific oligonucleotide probes are utilized, such as a TaqMan probe (Applied Biosystems. Foster City, Calif.), which includes a reporter fluorophore at the 5' end, and a quencher internally or at the 3' end. An exemplary 5' reporter fluorophore is FAM (5-carboxyfluorescein), and an exemplary 3' quencher fluorophore is TAMARA (6-carboxy-tetramethylrhodamine). The signal generated by the reporter fluorophore is detected, and quantitation of the amplicons can be made, such as by analysis of the resulting amplification curve.

Conventional thermocyclers use a thermoelectric heating element for active heating and cooling of a metal heater block that makes contact to plastic tubes containing 10-100 µL reactions. Heat transfer is made by conduction through the walls of the plastic tube. Thin walled tubes minimize heat transfer resistance in conventional thermocycling. Many innovative strategies have been conceived for more efficient heat transfer and amplification at accelerated speeds. Since PCR is widely used and many of its applications are highly urgent, it is desirable to decrease the reaction time. Thermocycling of the reaction mixture between three different temperatures is the most time-consuming portion of the entire process. Conventional PCR methods require several minutes per cycle, thus 1-2 hours for typical 30 cycles, due to limitations in conductive heating and cooling.

To increase the speed of DNA analysis by PCR, many researchers have focused on developing rapid thermocycling technologies to achieve thermal cycle times as low as 10 s per cycle (=5 min for typical 30 cycles; Zhang and Xing, *Nucleic Acids Research* 35, 4223-37, 2007; Roper et al., Analytical Chemistry 77: 3886-93, 2015; Farrar and Wittwer, Clinical Chemistry 61: 145-53, 2015). There are several limiting factors in achieving such extreme thermocycling speeds. The primary obstacle has been the need for instrumentation capable of rapid heat transfer. Heating elements must be made in high precision with substantial heating capacity. Laser-assisted heating has recently become quite popular, primarily to further speed up the heating time with extremely accurate temperature control. However, such equipment tends to be relatively bulky, quite expensive, and requires AC power, all of which are non-ideal for point-of-care diagnostics. The secondary obstacle has been the reaction volume. Reducing the reaction volume, typically in the range of nano- or even pico-liter scale, has been quite common in demonstrating rapid PCR assay, especially in lab-on-a-chip platforms. The smaller the volume, the faster the thermal cycling time becomes. However, with a 1 nL sample, one needs at least $10^6$ copies of genomic DNA per mL of sample (=$10^6$ cells/mL), which may not be possible in early detection of pathogens.

III. Devices and Methods of Use

Figure 1A:
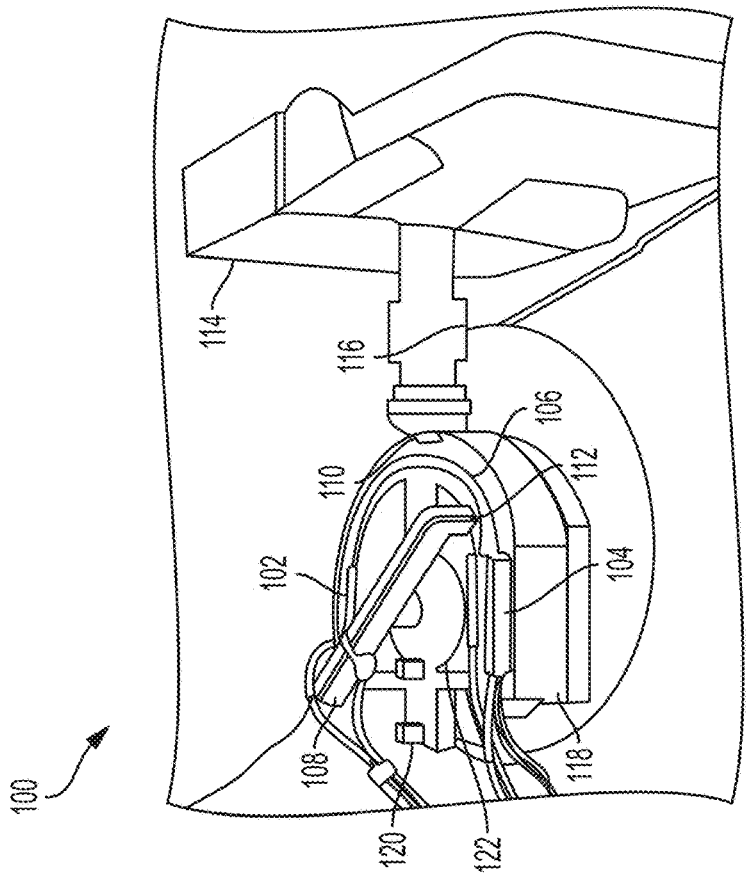

Disclosed herein are devices, systems and methods of use utilizing interfacial effects enabling droplet actuation, inhibition and early sensing of molecular reactions, such as of polymerase chain reaction. Referring to FIGS. 1A and 1B, a disclosed apparatus 100 includes a multichamber array comprising two chambers 102 and 104 containing a hydrophobic liquid, wherein a first chamber 102 of the two chambers comprises a heater and maintains the hydrophobic liquid at a temperature at or above the maximum temperature for a respective stage in thermocycling, and a second chamber 104 of the two chambers comprises a heater (shown as 103) and maintains the hydrophobic liquid at a temperature at or below the minimum temperature for a respective stage in thermocycling; a channel 106 for hydraulically connecting the two chambers and containing the hydrophobic liquid; a movement device, such as a motor arm 108 powered by a motor 122 wherein the movement device is adapted to move between the two chambers and along the channel 106; a droplet manipulating device coupled to the movement device 108 and immersed in the hydrophobic liquid, wherein the droplet manipulating device comprises a temperature sensing device configured to sense a temperature inside a droplet placed within the droplet manipulating device; and a controller 120, such as an IR photogate, operably connected to the movement device 108 and the temperature sensing device within the droplet manipulating device, the controller 120 being configured to command the movement device along the channel 106 based on the sensed temperature inside the droplet. In some examples, the temperature sensing device in the droplet manipulating device is a thermocouple 112, such as a looped thermocouple which may be bent (see FIG. 1C) such that a thermocouple junction is positioned inside the droplet. It is contemplated that the dimension of the chambers, choice of materials and choice of heating element may vary. In some embodiments, the device is designed to allow movement of one or multiple (e.g., one, two, three, four, five, six, seven or eight, including 2-8, up to 8) droplets of a desired volume (similar to conventional PCR, e.g. 10 µL, not nano- or pico-liter common in other rapid thermocycling methods) without touching the heater surface, bottom and side walls, as well as the oil-air interface during its operation. In some examples, the internal droplet temperature is used as a feedback signal for positioning of the droplet at the desired temperature region of the heat gradient. In some examples, the hydrophobic liquid is an inert hydrophobic oil (e.g., silicone oil). The hydrophobic liquid shapes a hydrophilic droplet into a spherical shape with the height-to-width ratio between 0.5 and 1.5, such as between 0.75 to 1.0 or 0.5 to 1.25 which facilitates manipulating the microdroplet. In some examples, the disclosed apparatus includes two chambers in between 90° to 180° from one another connected by an arced channel. A heat gradient (VT) is established across the arc so that all temperatures between two extremes (45-50° C. and 100-105° C.) are represented. In some examples, a viewing window, is positioned in between the two chambers, such as 90° from the two chambers.

In some examples, a disclosed device includes a chamber containing a hydrophobic liquid configured to maintain the hydrophobic liquid at a temperature at or above the maximum temperature for a respective stage in thermocycling; a channel hydraulically coupled to the chamber and extending from the chamber a distance sufficient to form a temperature gradient along the hydrophobic liquid; a movement device adapted to move along the channel; a droplet manipulating device coupled to the movement device and immersed in the hydrophobic liquid, wherein the droplet manipulating device comprises a temperature sensing device configured to sense a temperature inside a droplet placed within the droplet manipulating device; and a controller operably connected to the movement device and the temperature sensing device, the controller being configured to command the movement device along the channel based on the sensed temperature inside the droplet.

In some examples, the disclosed device includes a temperature sensing device which is a thermocouple 118. For example, in some examples the thermocouple is a looped thermocouple 112 which is configured so that a thermocouple junction is positioned inside the droplet. In some examples, a disclosed device includes a second temperature sensing device coupled to the movement device and configured to sense a temperature of the hydrophobic liquid. In some examples, the channel is arced. In some examples, the device further includes a transparent window 110 positioned between the two chambers, such as a transparent window 110 is positioned equidistant from the two chambers. In some examples, an image capture device 114 including a lens 116 is positioned in front of the transparent window 110 so that an image may be obtained through a viewing window within the device. In some examples, the image capture device is a smartphone. In some examples, the majority of components to a disclosed device are disposable and for one-time use. For examples, a disclosed device can include a disposable semicircular channel, motor arm, thermocouple, heating element, and silicone oil.

Also provided are methods of using a disclosed device. In some examples, methods of sensing molecular reactions are disclosed. In some examples, methods of amplifying a molecular target, such as a nucleic acid, are disclosed. In some examples, a method of amplifying a nucleic acid comprises dispensing a droplet into a thermocouple loop, wherein the thermocouple loop is immersed in a hydrophobic liquid with a temperature gradient; sensing a temperature inside the droplet; and moving the droplet along the temperature gradient according to a predetermined temperature profile for the droplet. In some examples, methods of controlling PCR amplification are provided. For example, the method can include dispensing a droplet containing a PCR cocktail into a thermocouple silhouette, wherein the thermocouple is configured to sense a temperature internal to the droplet; measuring an initial diameter of the droplet; thermocycling the droplet based on the temperature internal to the droplet; measuring a current diameter of the droplet between thermocycling cycles; and stopping the thermocycling responsive to a preset decrease in the current diameter of the droplet compared to the initial diameter of the droplet. In some examples, the disclosed device is utilized to control PCR amplification or to amply a nucleic acid in general. Thus, methods for monitoring progress of polymerase chain reaction or other molecular reactions by measuring interfacial tension or interfacial are provided herein. In some examples, methods for quantifying the initial concentration of a target gene by measuring the interfacial tension or interfacial effects of a reaction droplet over the course of thermocycling are provided. In some examples, methods for utilizing interfacial adsorption of contaminant molecules to minimize the need for sample preparation due to inhibition caused by such molecules are provided herein.

In some examples, the disclosed methods and/or device are used to diagnosis a subject with a particular condition and/or disease. In some examples, the disclosed methods and/or devices are used to determine a particular treatment regimen and/or efficacy of a treatment. For example, the disclosed methods and/or devices can be used in a wide variety of applications, including but not limited to, detecting and quantifying infectious agents in various settings, medical diagnostics, veterinary diagnostics, environmental monitoring, and general food safety. A list of potential users is as follows: (1) research laboratories (microbiology, food science, veterinary medicine, medicine, pharmacy, public health, biological/biomedical engineering, environmental science/engineering, etc.); (2) food industry (fresh produce, dairy products, meats, etc.); (3) hospital laboratories (disease diagnostics); (4) veterinary diagnostic laboratories; (5) environmental monitoring firms (e.g., air quality and water quality); (6) defense industry (e.g., biological warfare); and government agencies (e.g., NIH, EPA, CDC, USDA, DOD, etc.).

In one specific example, the disclosed device is used for ex vivo diagnosis of a condition, such as a tissue infection, by the rapid heating and cooling of a submerged reaction droplet suspended on a thermocouple. For example, the method comprises positioning a droplet on thermocouple (DOT) in a heated oil environment by a movement device, such as a motor, establishing a heat gradient (VT) across an arced channel between two heaters arranged at a configuration that allows the desired temperatures to be maintained; monitoring an internal temperature of the droplet, such as by use of a looped thermocouple (e.g., a bent, looped thermocouple); establishing a heat gradient at steady state within 10 minutes of commencing temperature ramping from room temperature (approximately 25° C.) under proportional-integral-derivative (PID) control of heater power; commencing droplet thermocycling when the droplet is dispensed onto the thermocouple loop at a 50° C. region of the gradient; and performing PCR by moving the droplet within the heat gradient and constantly moving the droplet back and forth within a temperature region until temperature targets are reached. In some examples of the disclosed method, heating rates up to 12° C./s for the droplet and 32° C./s for the oil are realized. In some examples, the duration of one cycle—including denaturation, annealing and extension—ranges from 48 to 28 s/cycle depending on the desired mode of operation. In some examples, the method further includes optimizing reaction conditions, such as to decrease cycle time adjusting offsets between the oil temperature and desired droplet temperature can be performed. In some examples of the method, the two heaters are arranged at 180° from one another, connected by an arced channel and the temperature extremes of 45-50° C. and 100-105° C. are maintained. In some examples, the method includes capturing an image of the DOT, such as by positioning an image capture device so that an image may be obtained through a viewing window within the device, such as a viewing window that is at 90° from the two heaters corresponding to the 70° C. region of the temperature gradient, thereby allowing the DOT to be imaged by the image capturing device (such as a camera). In some examples, PCR is performed in the presence of a detectable label, such as a detectable label associated with a fluorophore. In some examples, PCR is performed in the presence of a cyanine dye (e.g., SYBR Green, SYBR Green II, SYBR Gold, Oxazole Yello, Thiazole Orange or PicoGreen).

In some examples, the method includes quantitation of generated amplicons to provide a diagnosis and/or treatment recommendation. The change in the droplet height, resulting from the change in interfacial tension, would indicate the presence of specific nucleic acid sequence in the given sample. The threshold cycle number ($C_t$) can also be used to quantify the concentration of the nucleic acid sequence in the sample, using the pre-determined standard curve. For example, in some embodiments, once a patient's diagnosis is determined, an indication of that diagnosis can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, voltammetric trace, or other diagram), or an audible output.

In other examples, the output is a numerical value, such as an amount of a labeled amplicon in the sample as compared to a control, such as an amount of the amplicon in a subject not afflicted with the specific/condition being evaluated or an amount known to be representative of the amplicon in such subject. In additional examples, the output is a graphical representation, for example, a graph that indicates the value (such as amount or relative amount) of the detected amplicon in the sample from the subject on a standard curve. In a particular example, the output (such as a graphical output) shows or provides a cut-off value or level that indicates the presence of the specific condition/disease being evaluated. In some examples, the output is communicated to the user, for example by providing an output via physical, audible, or electronic means (for example by mail, telephone, facsimile transmission, email, or communication to an electronic medical record).

The output can provide quantitative information (for example, an amount of a measured molecule relative to a control sample or reference value) or can provide qualitative information (for example, a diagnosis regarding the condition/disease being evaluated).

In some examples, the output is accompanied by guidelines for interpreting the data, for example, numerical or other limits that indicate the presence or absence of the condition/disease being evaluated. The indicia in the output can, for example, include normal or abnormal ranges or a cutoff, which the recipient of the output may then use to interpret the results, for example, to arrive at a diagnosis, prognosis, or treatment plan. In other examples, the output can provide a recommended therapeutic regimen. In some examples, the test may include determination of other clinical information (such as determining the amount of one or more additional biomarkers in the sample).

In some embodiments, the disclosed methods of diagnosis include one or more of the following depending on the patient's diagnosis: a) prescribing a treatment regimen for the patient if the patient's determined diagnosis is considered to be positive for the condition evaluated; b) not prescribing a treatment regimen for the patient if the patient's determined diagnosis is considered to be negative for the condition evaluated; c) administering a treatment to the patient if the patient's determined diagnosis is considered to be positive for the condition evaluated; and d) not administering a treatment regimen to the patient if the patient's determined diagnosis is considered to be negative for the condition evaluated. In an alternative embodiment, the method can include recommending one or more of a)-d).

In some embodiments, a patient with a particular disease/condition or suspected of having such, can be pre-selected for the treatment and screening methods herein.

The following examples are provided to illustrate certain particular features and/or embodiments. These examples should not be construed to limit the invention to the particular features or embodiments described.

EXAMPLES

Example 1

Material and Methods

This example provides the materials and methods for the studies described in Example 2.
Polymerase Chain Reaction (PCR).

There are two different thermocycling modalities that are reported herein, and two different real-time detection modalities. The two thermocycling modalities are termed conventional thermocycling and droplet on thermocouple (DOT) thermocycling. The two real-time PCR (qPCR) modalities are termed commercial qPCR and droplet on thermocouple silhouette (DOTS) qPCR. There are four different target samples used. Vancomycin-sensitive *Enterococcus* (VSE, *Enterococcus faecalis* ATCC© 33186™) and vancomycin-resistant *Enterococcus* (VRE, *Enterococcus faecium* ATCC© 700221™) were propagated per the procedure outlined in the ATCC product sheet to $10^{-8}$ CFU/ml, pelleted by centrifugation at 6000×g for 10 min, resuspended in 100 μL molecular grade water and heatkilled at 95° C. for 15 min. *Escherichia coli* (Sigma; EC1-5G) was cultured in LB broth and genomic DNA was isolated with the gDNA DNeasy Blood & Tissue Kit (Qiagen, 69506). Purified *Klebsiella pneumoniae* strain 7026 genomic DNA was purchased from Zyptometrix. Three primer sets were used. The plasmid mediated antibiotic resistance gene vanA was targeted by the vanA primers: F: 5'-TCTGCAATAGA-GATAGCCGC-3' (SEQ ID NO: 1) and R: 5'-GGAGTAGC-TATCCCAGCATT-3' (SEQ ID NO: 2). The vanA amplicon is 377-bp in length. The amplicon length and primer pairing were confirmed by mapping to the VRE vanA gene (accession number AB247327 which is hereby incorporated by reference in its entirety as available of Oct. 24, 2014) [vanA seq]. The 16s rRNA gene was targeted at hypervariable regions V3 and V1-V2. The V3 primer sequences are F: 5'-ACTCCTACGGGAGGCAGCAG-3' (SEQ ID NO: 3) and R: 5'-ATTACCGCGGCTGCTGG-3' (SEQ ID NO: 4) yielding an amplicon length of 196-bp. The V1-V2 primer sequences are F: 5'-AGAGTTTGATCMTGGCTCAG-3' (SEQ ID NO: 5) and R: 5'-CYIACTGCTGCCTCCCGTAG-3' (SEQ ID NO: 6) for an amplicon length of 353-bp. The PCR recipe varies by modality, but the standard PCR recipe is used for most studies and unless otherwise noted. The standard PCR cocktail was made up of the following components: PCR master mix [GoTaq Green Master Mix 2× (Promega; M7122) or Fast SYBR Green Master Mix 2× (Applied Biosystems; 4385612)], forward and reverse primers (10 μM), target, and nuclease-free water. The components were in the proportions, 5:1:1:3 respectively. The target proportion was increased for the heart valve tissue biopsy by reducing the water portion. The real-time detection modalities (commercial qPCR and droplet silhouette detection) use modified PCR cocktails.
Design and Fabrication of DOTS qPCR Device.

The mechanical aspects of the device were designed using computer aided design software (SolidWorks) and custom parts were 3D printed out of acrylonitrile butadiene styrene (ABS) polymer (Dimension uPrint SE). Nickel-chromium heating wire (Omega; NI60-010-200) with a resistance per length of 6.750 Ω/ft was wound in a serpentine fashion to a final resistance of 10Ω and pressed between two 25×19 mm sections of double-sided solvent-resistant tape (McMaster-Carr; 75955A672) such that the wire did not make self contact. Single sided adhesive Teflon (McMaster-Carr; 8711 K22) was applied to the top surface of the heater assembly to minimize fouling. A heater was bent into the ends of the heat gradient chamber and secured to the bottom and sides with quick cure glue (Gorilla Glue; 39038). The ends of the heater wire were connected to the PID controller via copper wire. A 36-gauge k-type thermocouple (Omega; 5TC-TT-K-36-36) was mounted 5 mm above the surface of both heaters to serve as a feedback control. The PID controller was custom designed to regulate the 7.5 V, 0.75 A heater power supply. Alternatively, instead of using heater wire, a Peltier device could be used. The chamber was filled with 8 mL silicone oil (Santa Cruz Biotechnology; sc-215854A). Temperature setpoints for the heat gradient extremes (101° C. and 50° C.) were equilibrated at steady state within 10 min of commencing temperature ramping. A heat gradient was established between the temperature extremes and verified by a thermocouple traveling at 17.6°/s around the chamber arc. All temperatures between the two setpoints are represented. It is contemplated that the following components of the device are disposable and meant for one-time use: the semicircular channel, motor arm, thermocouple, heating element, and silicone oil.

A thermocouple to be used for droplet suspension was bent into a loop with a diameter of 3 mm with the junction bent downward below the center of the loop. The thermocouple loop was mounted on the motor arm hanging such that it is completely submerged below the surface of the oil. The thermocouple loop can be used for droplet positioning feedback and for recording reaction temperatures over the course of the reaction. Each thermocouple was used only for a single sample, after which it was discarded to avoid contamination and non-specific amplification. A miniature motor (NMB Technologies; PG15S-D20-HHB9) with 0.1760 step angle was fixed concentric to the heat gradient chamber arc. The motor was powered directly from microcontroller (Arduino Mega) power supply and is controlled by a motor controller circuit assembly (Sparkfun Electronics; Easydriver). The zero position corresponds to the site of the viewing window and is calibrated using an IR photogate.

An optically transparent fused silica window (Edmund Optics; #45-309) separates the oil from the lens of the smartphone camera. This window created a view into the channel at the 70° C. region of the heat gradient. An adjustable lens tube (ThorLabs; SM05V05) containing an N-BK7 piano-convex lens (ThorLabs; LA 1560) focused the image on the smartphone camera (Apple iPhone 4) at a focal point 22.7 mm from the back planar surface of the lens. The lens tube was connected to the smartphone via a custom designed smartphone housing that aligns the lens with the smartphone camera.

Thermocycling.

Conventional thermocycling was conducted on the MJ Research Minicycler. One cycle consists of the following three phases, denaturation for 30 s at 95° C., annealing for 30 s at 58° C. and extension for 40 s at 72° C. In order to analyze samples at increments of 5 cycles from 0 to 30 cycles, seven replicate PCR cocktails were prepared. The 0 cycle sample was not thermocycled. The remaining six samples were thermocycled for 5 cycles at a time, removing one sample from the thermocycler every 5 cycles and storing in the 4° C. refrigerator. For samples that are cycled uninterrupted for 30 cycles, a 3 min initial denaturation step at 95° C. and a 10 min final extension step at 72° C. were added.

Droplet on Thermocouple (DOT) Thermocycling.

5-10 µL of PCR cocktail were dispensed onto the thermocouple loop by micropipette such that the droplet was completely submerged in the heated oil. The droplet was dispensed with the motor arm positioned at the low temperature region to avoid non-specific extension prior to initial denaturation and annealing. Temperature setpoints for each phase of the reaction (denaturation, annealing, and extension), phase duration, and cycle numbers were programmed in order that the device operates automatically. The device can be run in multiple different modes. Droplet position can be determined either by predefined temperature mapping or by real-time temperature feedback from the thermocouples mounted on the motor arm, which measure oil and droplet temperatures simultaneously. For temperature feedback, the thermocouples mounted on the motor arm measure the oil and droplet temperatures. The device was reprogrammable to facilitate thermocycling attributes such as extended initial denaturation, final extension and touchdown PCR. Under typical thermocycling, the droplet was never held stationary so that the continuous movement enhances heat transfer by convection.

Gel Electrophoresis.

The PCR products were analyzed by gel electrophoresis. 3% w/v agarose gel (Sigma; A0169) in 1× tris-acetate-EDTA (TAE) buffer (Invitrogen; 24710-030) was used for amplicons between 100 and 500-bp. 4 µL sample added was added to each lane and a 1 kb-plus DNA ladder (Invitrogen; 10787) was used as a length standard. An electrophoresis power supply (Fischer Scientific; FB200) provided a potential of 120V for 40 minutes. The gels were stained with ethidium bromide (Sigma; EIS10), washed with 1×TAE and imaged under UV irradiation. Images were analyzed with ImageJ software (U.S. National Institutes of Health).

Real-Time PCR on Commercial Device and Standard Curve Construction.

A real-time PCR (qPCR) standard curve was constructed on the StepOne Real-Time PCR System (Applied Biosystems; 4376374). The PCR cocktail contained 25 µL of Fast SYBR Green Master Mix (Applied Biosystems; 4385612), 1 µL of forward and reverse primers (10 µM each), 1 µL of target DNA, and 23 µL of nuclease-free water, for a total volume of 50 µL. The thermocycler was programmed for 40 cycles of 95° C. for denaturation and 60° C. for annealing, followed by the dissociation protocol. PCRs were run in triplicate for each initial target amount (No) using 10-fold serial dilutions of the *Klebsiella pneumoniae* strain Z026 genomic DNA from $1.5 \times 10^2$ to $1.5 \times 10^5$ genomic copies. The number of genomic copies was estimated using a genomic mass of 5 fg. A fluorescence threshold ($F_t=1.0$) was chosen within the exponential phase of amplification, and the $C_t$ values were calculated using the StepOne software. The logarithm of $N_0$ was plotted against the average $C_t$ value for each No, and a trend line was established for this plot using linear regression analysis: $\log(No)=-0.278C_t+12.1$. The slope $[-\log(E+1)]$ was used to calculate the slope-derived efficiency ($E_S=89.5\%$), and the y-intercept $[\log(N_t)]$ was used to determine the number of amplicons at $F_t$ ($N_t=1.15 \times 10^{12}$ copies).

Porcine Model for Infective Endocarditis.

A porcine heart was procured. The aortic, mitral, and tricuspid valves were excised from the heart under sterile conditions. 6 mm circular sections were cut using a skin biopsy punch. The valve sections were kept in a 12 well tissue culture plate in antibiotic containing M199 tissue culture media overnight at 4° C. to ensure sterility. For cryopreservation, valve sections were transferred to M199 tissue culture media with 10% glycerol. The cryovials were placed in a Nalgene 1° C. freezing container and placed into the −40° C. freezer overnight. After freezing the cryovials were transferred to a freezer box. To prepare the tissue samples for PCR, valve sections were defrosted, the tissue culture media was removed, and the tissue was washed twice with nuclease-free water. The sections were inoculated with 10 µL of vancomycin-resistant *Enterococcus* (VRE, *Enterococcus faecium* ATCC© 700221™) suspended in nuclease-free water at 109 CFU/ml and 10 µL of nuclease-free water was added. Debridement was simulated by grinding the inoculated tissue with a micro mortar and pestle (BioMasher II) for 1 min. The liquid phase of the ground tissue was pipetted to be used as is for PCR target without further purification. To evaluate the inhibition effect of the tissue contamination, the Applied Biosystems ABI Prism 7000 Sequence Detection System was used, and the $C_t$ values were calculated with an $F_t$ of 1.0.

Protein Quantification.

The Bradford assay (Quick Start Bradford Protein Assay, Bio-Rad) was used to determine the protein content of the tissue sample after grinding. Standard curves were created for the assay using bovine serum albumin (BSA) and gamma globulin. The protein content of the tissue sample was estimated as a range using the BSA standard curve as the lower limit and the gamma globulin standard curve as the upper limit. BSA has a higher affinity for the Bradford dye than gamma globulin.

Interfacial Tension (γ) Measurement.

The interfacial tension was measured by the pendant droplet method on an FTÅ 200 contact angle and interfacial tension analyzer (First Ten Angstroms). Pendant droplets were extruded from an 18-gauge blunt needle tip (Jensen Global; JG18) with an inside diameter of 0.9652 mm, and interfacial tension measurements were made at droplet equilibration at 2, 4, and 6 min after extrusion. The average interfacial tension, along with the standard error, was plotted.

Droplet on Thermocouple Silhouette Real-Time PCR (DOTS qPCR).

Real-time detection of PCR amplification was achieved by analyzing the droplet-on-thermocouple silhouette during thermocycling. A special PCR cocktail was formulated to aid in the visualization of the droplet-on-thermocouple silhouette. This cocktail contains Fast SYBR Green Master Mix, GoTaq Green Master Mix, forward and reverse primers (10 µM), target, and nuclease-free water in the proportion 5:1:1:1:2. For 0-15 cycles, the droplet was positioned in front of the viewing window, which is located at the 70° C. region of the heat gradient. The image of the droplet was captured by a smartphone camera (Apple iPhone 4) every 5 cycles, and the droplet height at the center was determined by analysis with the ImageJ software. The percent decrease in droplet height with respect to the droplet height at cycle zero was plotted against the cycle number.

Example 2

This example describes an exemplary DOTS qPCR device and methods of use.

DOTS qPCR Device.

The DOTS qPCR device (FIGS. 1A and 1B) is designed to enable deployed as a point-of-care diagnostic tool and to epitomize simplicity, small form factor, mobile integration, and disposability. In some examples, the device allows for ex vivo diagnosis of tissue infections by the rapid heating and cooling of a submerged reaction droplet suspended on a thermocouple. The droplet-on-thermocouple (DOT) (FIG. 1C) is submerged in a heated oil environment and is positioned by a motor (FIGS. 1D-F). The oil is contained within a semicircular channel with two heaters, located at 0° and 180°, which maintain the two temperature extremes (45-50° C. and 100-105° C.). A heat gradient is established along the channel with temperatures between the two extremes being represented (FIG. 2A). From room temperature (25° C.), the steady state of the heat gradient is established within 10 minutes of commencing temperature ramping using proportional-integral-derivative (PID) control of the heater power (FIG. 2B). At the midpoint of the channel, a viewing window allows macroscopic imaging of the droplet by a smartphone camera with an attached lens. The oil temperature at this window is 70° C. The internal temperature of the droplet is continuously monitored by a thermocouple, which is bent such that the thermocouple junction is positioned inside the droplet (FIG. 1C). The position of the droplet within the heat gradient is accurately controlled using real-time feedback of its internal temperature.

Non-specific amplification is avoided by dispensing the droplet onto the thermocouple loop at the 50° C. region of the gradient. Rapid thermocycling is then conducted by continuously moving the droplet within the heated oil until the desired temperature is reached (FIGS. 1D-F). This continuous movement enhances the thermal transfer since it provides forced convection between the droplet and the oil. By this technique, droplet ramp rates up to 12° C./s and oil ramp rates up to 32° C./s are achieved (FIG. 2C). Thermal cycle times range from 28 to 48 seconds, depending on the desired mode of operation. The thermocycling temperature profiles indicate that reaction temperatures are consistently achieved in each cycle (FIG. 2C). The droplet temperatures at each phase are 90.4±0.2° C. for denaturation, 68.4±0.2° C. for extension, and 60.2±0.2° C. for annealing. The accuracy of the temperature control is ensured by real-time droplet temperature feedback.

In order to decrease thermal cycle times, increased offsets between the oil temperature and the desired droplet temperature ($T_{oil} - T_{droplet}$) are used to enhance convective heat transfer. Convective heat transfer is governed by the equation, $q = h(T_\infty - T_{object})$, where q is heat flux, h is the heat transfer coefficient, $T_\infty$ is the temperature of the surrounding medium (the oil), and $T_{object}$ is the temperature of the object being heated (the droplet). To achieve the temperature offsets, the droplet is positioned at oil temperatures higher than the desired droplet temperature during heating and at oil temperatures lower than the desired droplet temperature during cooling (FIG. 2C). Greater offsets yield a more rapid rate of heat transfer, and droplet temperature feedback is used to mitigate the risk of overshoot. Using this thermocycling strategy, reproducible amplification of the hypervariable region V3 of the 16S rRNA gene was obtained from 7 pg purified *Klebsiella pneumoniae* genomic DNA (equivalent to $1.4 \times 10^3$ genomic copies) at thermocycling speeds of 48 s/cycle (FIG. 2D). The coefficient of variation of the three band intensities, representing three separate amplifications, is 4.0%, indicating a high degree of consistency between measurements. The absence of a band for the no template control (NTC) (FIG. 2D) indicates that the device is not susceptible to DNA contamination, which could lead to false positives.

Interfacial Adsorption of Contaminating Tissue Proteins

Figure 3C:
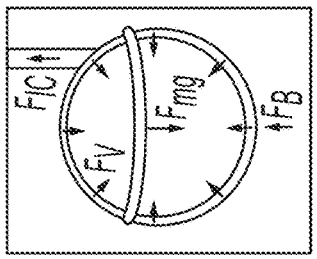
FIG. 3C is a free-body force diagram with the interfacial layer shown in clear. The forces on the droplet include the interfacial tension force ($F_\gamma$), the buoyancy force ($F_B$), the weight of the droplet ($F_{mg}$), and the thermocouple force ($F_{TC}$).
Figure 3F:
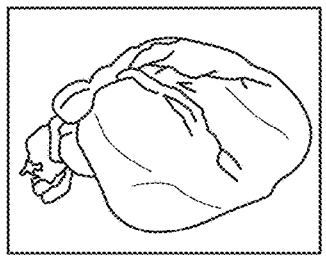
FIGS. 3F and 3G are digital images of a porcine heart from which aortic, mitral and tricuspid valves were excised, sectioned, inoculated, ground and used in PCR reactions.
Figure 3G:
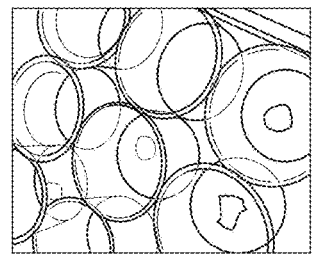
Figure 3B:
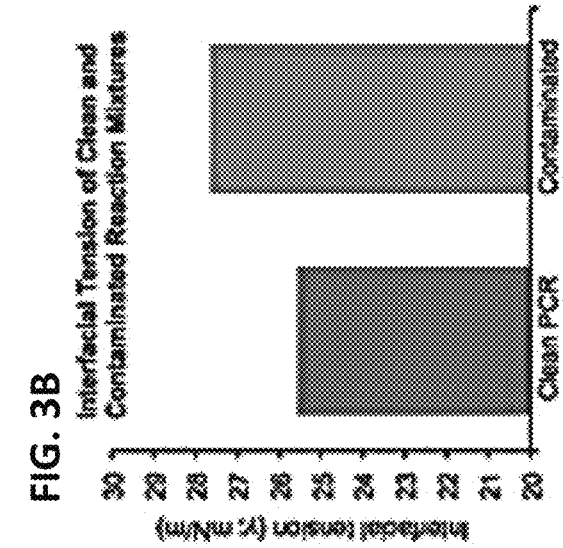
FIG. 3B is a graph of interfacial tensions (γ) of clean and contaminated PCR mixtures are 25.55 mN/m and 27.60 mN/m, respectively.
Figure 3E:
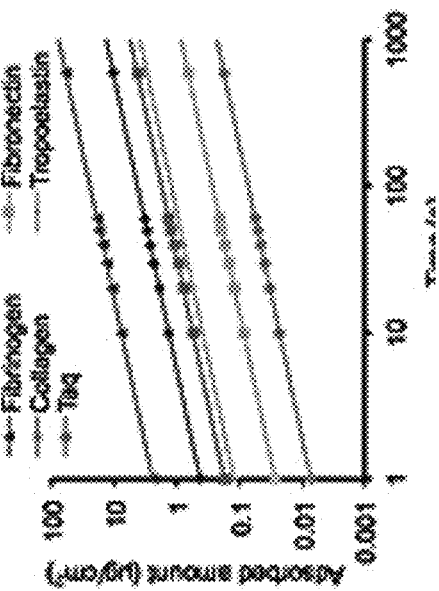
FIG. 3E illustrates protein diffusion to the interface calculated based on typical blood and tissue concentrations using diffusivities from literature and Fick's equation. For comparison, the diffusion of Taq polymerase to the interface is also calculated.
Figure 3A:
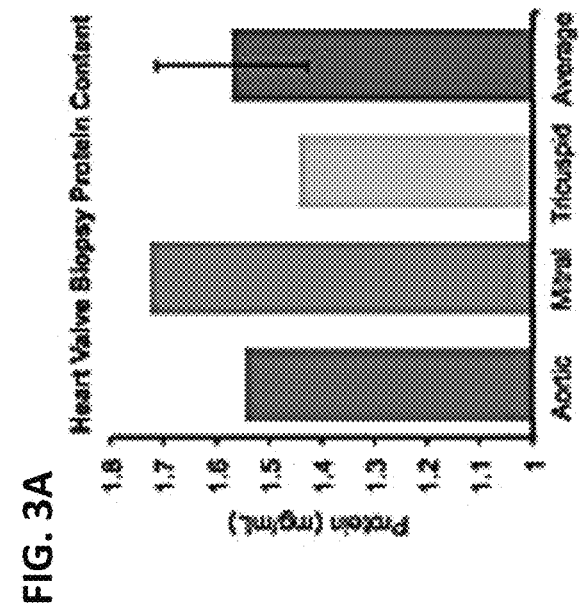
FIG. 3A is a graph of the protein concentrations of the aortic, mitral, and tricuspid valve sections excised from a porcine heart and ground using a micro-mortar and -pestle. The total protein concentration of the tissue model was 1.6-0.1 mg/mL.
Figure 3D:
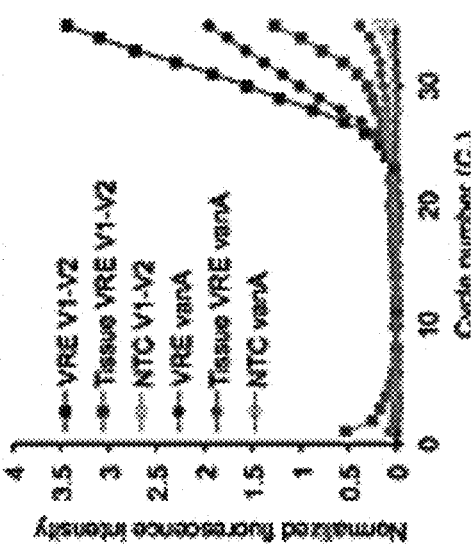
FIG. 3D provides fluorescence qPCR amplification curves for 16S rRNA hypervariable regions V1-V2 and vanA gene from intact vancomycin-resistant $Enterococcus$ $faecium$ (VRE) with and without tissue contamination. The $C_t$ values for 16S rRNA V1-V2 without tissue, 16S rRNA V1-V2 with tissue, vanA without tissue, and vanA with tissue are 28.4, 30.0, 34.0, and 39.4, respectively. The tissue contamination inhibits fluorescence qPCR, as seen by the upward shift of 1.6 cycles for the 16S rRNA V1-V2 target and 5.4 cycles for the vanA target. Additionally, NTC samples for each primer set are plotted.

A porcine model for IE was developed (FIG. 3F). Excised heart valve tissue punches (6 mm diameter sections) (FIG. 3G) were sterilized, inoculated with vancomycin-resistant *Enterococcus faecium* (VRE), and ground using a micromortar and -pestle. The liquid phase of the tissue after grinding had a protein concentration of 1.6±0.1 mg/mL (FIG. 3A). The interfacial tensions (γ) of the PCR cocktail with the purified target and the PCR cocktail with the tissue-contaminated target were measured with a First Ten Ångstroms (FTÅ) 200 contact angle and interfacial tension analyzer, and the interfacial tensions were 25.55 mN/m and 27.60 mN/m, respectively (FIG. 3B). A free-body force diagram illustrates the direction of the forces acting on the droplet-on-thermocouple (FIG. 3C). Due to the interfacial tension force $F_\gamma$, a droplet of the PCR mixture can be suspended on the thermocouple loop. In fluorescence qPCR, tissue proteins inhibit amplification of the 16S rRNA gene V1-V2 hypervariable regions and the antibiotic resistance gene vanA from intact VRE. Therefore, the threshold cycles ($C_t$) are shifted upward by 1.6 cycles for the 16S rRNA V1-V2 reaction and by 5.4 cycles for the vanA reaction (FIG. 3D). In DOT thermocycling, these tissue proteins should be adsorbed at the oil-water interface, so that contaminating proteins are effectively eliminated from the PCR (interfacial compartmentalization). However, Taq polymerase should not be adsorbed at the oil-water interface. Therefore, the diffusion amounts of the relevant blood and tissue proteins to the oil-water interface were calculated for comparison with the diffusion of Taq polymerase (FIG. 3E).

The following proteins were included in the calculation, with the corresponding molecular weights and diffusivities: albumin (94 kDa, $6.1 \times 10^{-7}$), immunoglobulin-G (150 kDa, $4.0 \times 10^{-7}$ cm$^2$/s), fibrinogen (340 kDa, $2.0 \times 10^{-7}$ cm$^2$/s), fibronectin (450 kDa, $0.9 \times 10^{-7}$ cm$^2$/s), collagen type 1 (282 kDa, $0.78 \times 10^{-7}$ cm$^2$/s), tropoelastin (65 kDa, $4.6 \times 10^{-7}$ cm$^2$/s), and Taq polymerase (94 kDa, $4.7 \times 10^{-7}$ cm$^2$/s). As shown in FIG. 3G, the adsorbed amounts of albumin and fibrinogen are several orders of magnitude greater than that of Taq polymerase.

Amplification Performance of Droplet-On-Thermocouple (DOT) Thermocycling.

Vancomycin-resistant *Enterococcus faecium* (VRE) and vancomycin-sensitive *Enterococcus faecalis* (VSE) were successfully distinguished based on amplification of a 377 bp segment of the vanA gene directly from bacterial culture using DOT thermocycling (FIG. 4A). This band was absent for the no template control (NTC) sample. A sub-picogram limit of detection (LOD) was established for amplification of the 196 bp 16S rRNA V3 amplicon from 0.7 pg *K. pneumoniae* genomic DNA (equivalent to $1.4 \times 10^2$ genomic copies) at 48 s/cycle (FIG. 4B). Moreover, the plasmid-mediated antibiotic resistance gene vanA was amplified directly from the inoculated heart valve tissue (FIG. 4C, lane 1). The inoculum contained $7 \times 10^5$ colony-forming units (CFU) of VRE, which is in the concentration range relevant to IE vegetations. The inoculated heart valve tissue was ground with micro-mortar and -pestle, and the liquid phase was pipetted directly into the PCR cocktail without further purification. Despite inhibitions observed on the fluorescence qPCR instrument, amplification in the presence of protein contamination was achieved, because of interfacial compartmentalization (leading to inhibition relief). The 16S rRNA V3 region was successfully amplified from the inoculated heart valve tissue at thermocycling speeds of up to 28 s/cycle or 14 min/30 cycles (FIG. 4C, lanes 2-4).

Real-Time Detection by Analysis of Droplet-On-Thermocouple Silhouette.

Figure 5A:
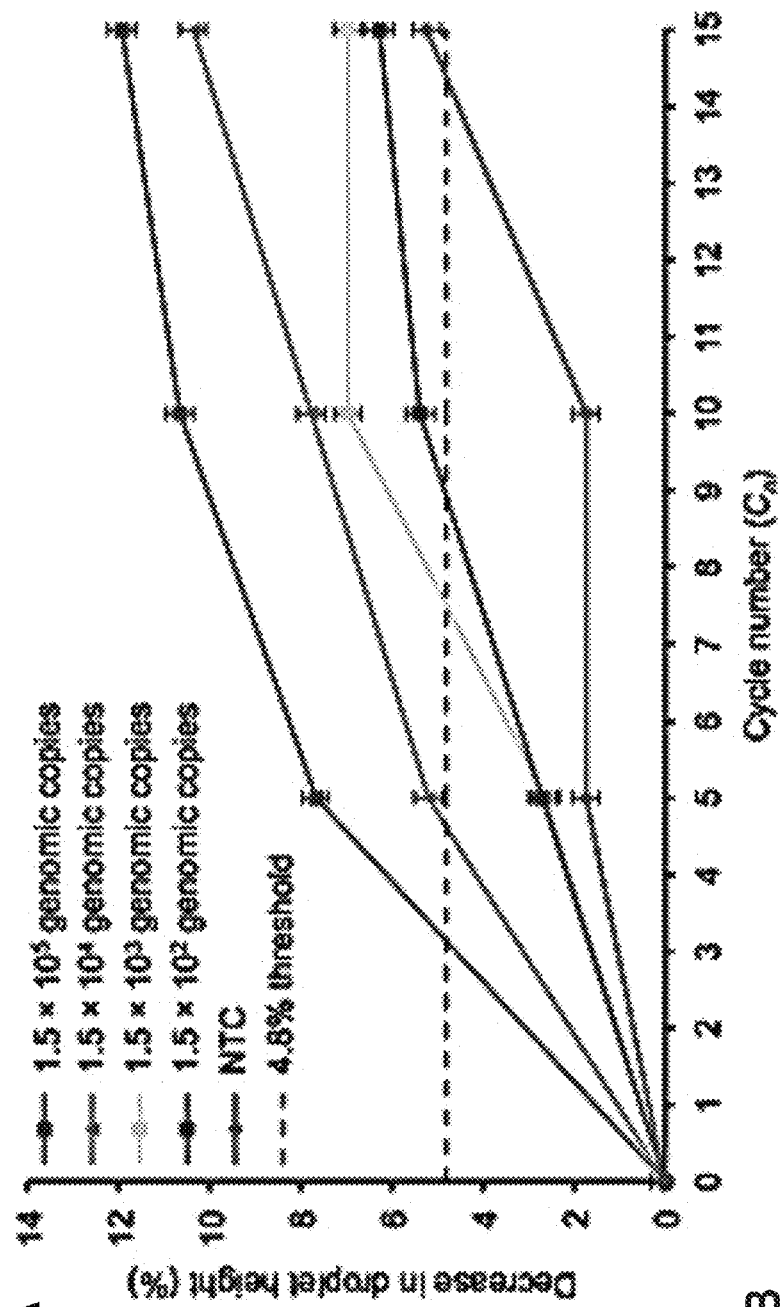
FIG. 5A is a graph of real-time detection of 16S rRNA amplification during early cycles by DOTS qPCR at a thermocycling speed of 48 s/cycle. Percent decrease in droplet height was plotted against $C_n$ for amplifications from 750, 75, 7.5, and 0.75 pg genomic DNA ($1.5 \times 10^5$, $1.5 \times 10^4$, $1.5 \times 10^3$, and $1.5 \times 10^2$ genomic copies, respectively) and no template control (NTC). Error bars represent overall device noise. A 4.8% threshold for detection is also plotted. The threshold was chosen to optimize the $R^2$ value of the linear regression shown in FIG. 8.

PCR amplification was observed in the presence of SYBR Green I (SG) by DOT thermocycling is accompanied by a change in droplet volume, which is measured as a change in droplet height from the initial value before thermocycling. The change in volume is observed through the viewing window at the 70° C. region of the heat gradient. Images are captured by the smartphone camera every 5 cycles (FIG. 5B), and the droplet-on-thermocouple silhouette is used for droplet height measurements. During the early thermal cycles, the decrease in droplet volume is dependent on the initial DNA amount ($N_0$) of the reaction (FIG. 5A). In FIG. 5A, the percent decrease in droplet height is plotted against the cycle number ($C_n$) for $N_0$ values ranging from $1.5 \times 10^2$ to $1.5 \times 10^5$ genomic copies. The error bars of the droplet height measurements represent the overall device noise, which was determined by loading consecutive 7.5 µL droplets onto the thermocouple loop, positioning the droplet-on-thermocouple at the viewing window, imaging the droplet with the smartphone camera, and measuring the standard error of the droplet height measurement. The detection threshold (4.8% decrease in droplet height) is also plotted in the figure to illustrate how $C_t$ can be calculated by linear interpolation between two measured values. The threshold value of 4.8% was chosen to optimize the $R^2$ value of the standard curve linear regression.

Decrease in Interfacial Tension During Amplification in the Presence of SYBR Green I.

Figure 6A:
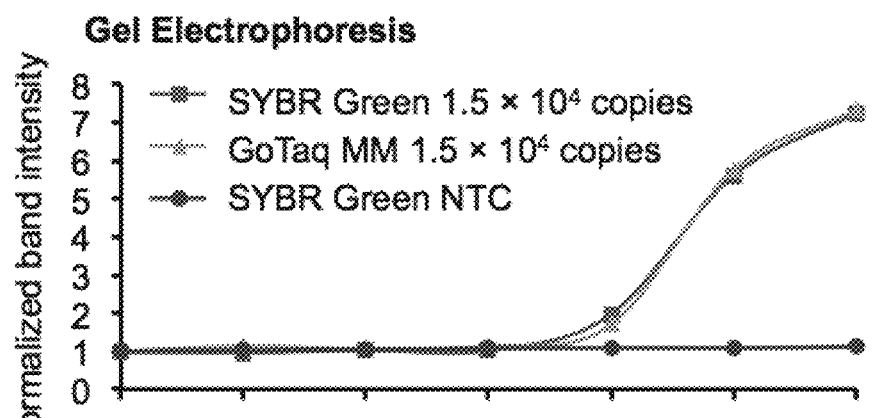
FIGS. 6A-6C illustrate interfacial tension during DNA amplification in the presence of SYBR Green. Three reactions with different conditions were thermocycled in increments of five cycles. The reaction conditions were 1) 75 pg K. pneumoniae genomic DNA ($1.5 \times 10^{4}$ genomic copies) with SYBR Green I (SG) to amplify the 16S rRNA V3 amplicon (196 bp), 2) 75 pg K. pneumoniae genomic DNA ($1.5 \times 10^4$ genomic copies) without SG to amplify the 16S rRNA V3 amplicon (196 bp), and 3) no template control (NTC) with SG. The samples were analyzed by gel electrophoresis.

To compare the interfacial tension of PCR mixtures during amplification with the signals from gel electrophoresis and fluorescence qPCR, the following experiments were performed. First, a PCR with $1.5 \times 10^4$ genomic copies was conventionally thermocycled with SG in increments of 5 thermal cycles, and the amplification was analyzed by gel electrophoresis. Another PCR with the same $N_0$ ($1.5 \times 10^4$ genomic copies) was similarly thermocycled but in the absence of SG. A third PCR lacking target DNA (NTC) was thermocycled with SG, and no amplification was detectable by gel electrophoresis even after 30 thermal cycles. The band intensities on the gel electropherograms were quantified at the expected product length (196 bp), normalized to the band intensity at $C_0$, and plotted against $C_n$ (FIG. 6A). DNA amplification was detected after 20 thermal cycles by gel electrophoresis and after 21.11±0.06 thermal cycles by fluorescence (FIG. 6B) for the reactions with $N_0$ of $1.5 \times 10^4$ genomic copies. No amplification was detected for the NTC reaction with SG by gel electrophoresis or by fluorescence.

The interfacial tension γ during the three different reactions was measured every 5 thermal cycles with a First Ten Ångstroms (FTÅ) 200 contact angle and interfacial tension analyzer. The change in interfacial tension with respect to the interfacial tension at $C_0$ ($d\gamma/\gamma_0$) was plotted against $C_n$ (FIG. 6C). The interfacial tension of the SG reaction with amplification decreased by 21% by $C_{10}$, after which it remained nearly constant. On the other hand, the interfacial tension of the SG NTC reaction increased by 6% at $C_5$ and thereafter subsequently fluctuated within 4% of no change. The interfacial tension of the reaction with amplification but without SG increased by 11% at $C_5$ and then increased to 19% by $C_{30}$. The only reaction condition that resulted in an appreciable decrease in the interfacial tension as a function of $C_n$ was the combination of SG and an increasing DNA concentration (FIG. 6C). Interestingly, after DNA amplification by PCR in the presence of SG, colloidal suspensions within the oil phase were observed by light microscopy (FIG. 7A). These water-in-oil droplets have a volume of 0.5-4.2 fL and a corresponding diameter of 1-2 µm.

Low Threshold Cycle Detection by DOTS qPCR.

Figure 8B:
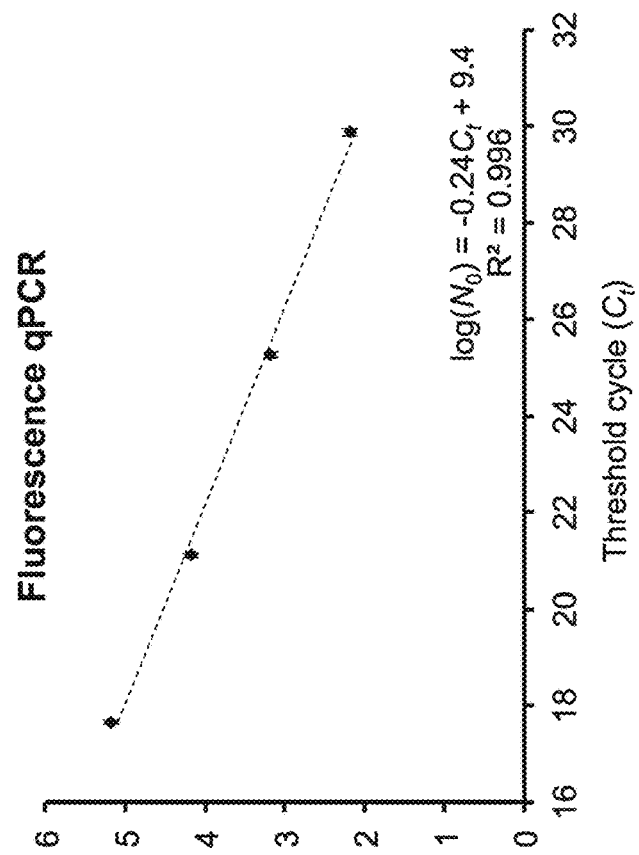
FIGS. 8A and 8B provide real-time PCR standard curves for DOTS qPCR and fluorescence qPCR.
Figure 8A:
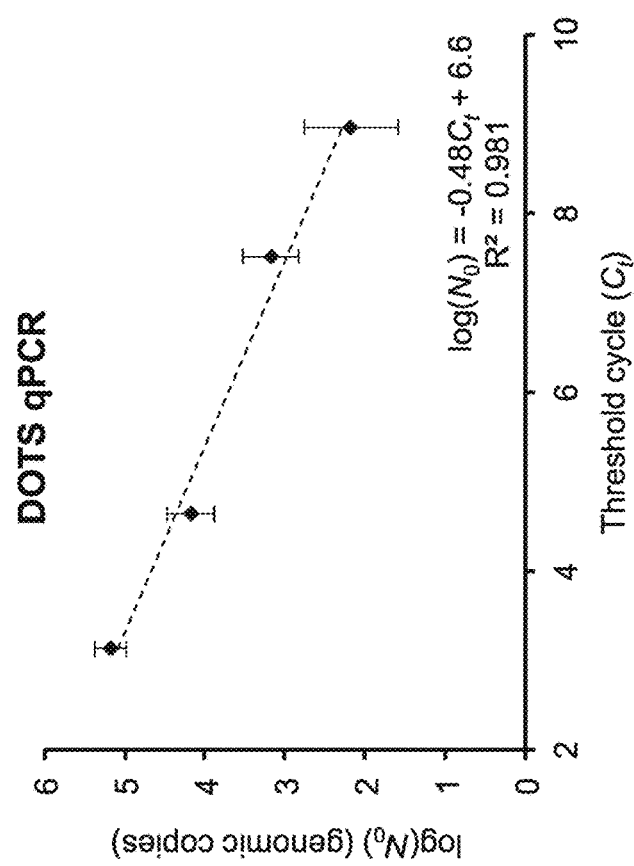

In order to establish a standard curve, the logarithm of the initial DNA amount [log(No)] is plotted against the threshold cycle $C_t$ in FIGS. 8A and 8B. The threshold cycle is defined as the theoretical fractional thermal cycle at which the detection threshold is reached. The detection threshold for DOTS qPCR (FIG. 8A) was set at a 4.8% decrease in droplet height, and the $C_t$ values were calculated by linear interpolation between two measured values. For fluorescence qPCR (FIG. 8B), the detection threshold was set at 1.0, and the $C_t$ values were calculated using the StepOne Real-Time PCR software (Applied Biosystems; 4376374). The $C_t$ values for DOTS qPCR and fluorescence qPCR for $N_0$ values ranging from $1.5 \times 10^2$ to $1.5 \times 10^5$ genomic copies and for NTC are reported in Table 1. The linear relationship between the initial DNA amount and the threshold cycle for DOTS qPCR was determined to be $\log(No) = -0.48C_t + 6.6$, with an $R^2$ of 0.981. The similar linear relationship for fluorescence qPCR is $\log(No) = -0.24C_t + 9.4$, with an $R^2$ of 0.996. On average, quantification by DOTS qPCR can be done 17.53 cycles earlier than is possible using fluorescence qPCR. At a thermocycling speed of 48 s/cycle, DOTS qPCR can detect $1.5 \times 10^5$ genomic copies of bacterial DNA in 2 min 30 s and $1.5 \times 10^2$ genomic copies in 7 minutes, 10 seconds, whereas a negative result confirmed in 11 minutes, 31 seconds.

TABLE 1

Threshold cycles for DOTS qPCR and fluorescence qPCR. Uncertainties have been determined as the standard error of repeated measurements for DOTS qPCR and as the standard error of triplicate experiments for fluorescence qPCR.

| $N_0$ (genomic copies) | DOTS qPCR $C_t$ | Fluorescence qPCR $C_t$ |
|---|---|---|
| $1.5 \times 10^5$ | $3.1 \pm 0.2$ | $17.66 \pm 0.04$ |
| $1.5 \times 10^4$ | $4.6 \pm 0.3$ | $21.11 \pm 0.06$ |
| $1.5 \times 10^3$ | $7.5 \pm 0.4$ | $25.28 \pm 0.07$ |
| $1.5 \times 10^2$ | $9.0 \pm 0.6$ | $29.88 \pm 0.03$ |
| NTC | $14.4 \pm 0.4$ | $32.4 \pm 0.1$ |

With DOTS qPCR, real-time quantification of nucleic acids is possible for $1.5 \times 10^5$ genomic copies of bacterial DNA within 3 minutes 30 seconds (2 minutes 30 seconds for thermocycling and 1 minute for sample preparation/loading). The enabling features of our novel methodology stem from interfacial effects, with the droplet stability ensured by the centrally acting interfacial tension ($\gamma$) forces. While miscellaneous tissue components are found to inhibit fluorescence qPCR (FIG. 3D), minimal sample preparation is necessary with DOT thermocycling because these inhibitory components are sequestered at the oil-water interface (FIG. 3E). The surrounding oil environment also prevents droplet evaporation. To achieve accurate thermocycling, reaction droplets are positioned within the oil heat gradient by a feedback-controlled motor, and thermal cycle times are as short as 28 s (FIG. 4C). Furthermore, PCR amplification is detected during the early cycles because changes to the interfacial composition lead to a decrease in droplet volume. Therefore, DOTS qPCR does not require extensive thermocycling to reach the detection threshold (FIG. 5).

Inhibition Relief by Interfacial Adsorption of Contaminant Proteins.

An interfacial tension increase was observed upon the addition of contaminant proteins to the PCR mixture (FIG. 3B). This represents a change in the interfacial composition of the droplet due to protein diffusion to the interface (FIG. 3E). Because of their relatively high concentrations and diffusivities, the relevant blood and tissue proteins will diffuse to the interface before the Taq polymerases. Proteins adsorb strongly at and stabilize the oil-water interface by a three-part process (FIG. 7B a-c)—enhanced by thermal induction of unfolding—1) protein adsorption, 2) conformational change, and 3) aggregation. This process follows the Vroman effect and has been widely studied because of its implications in pharmaceutical and food industries. Moreover, Taq polymerase is thermally stable and will not become denatured during heating, whereas tissue proteins are not stable at PCR temperatures and will become denatured. Protein denaturation exposes hydrophobic residues, which increases the affinity of the protein for the oil-water interface. Without the oil-water interface, the presence of protein inhibits PCR (FIG. 3D). The interfacial adsorption described here relieves PCR inhibition and offers the potential to eliminate DNA isolation from the PCR workflow.

Association of SYBR Green with DNA to Render Amplicons Hydrophobic.

Interfacial tension is responsible for droplet-on-thermocouple stability because the centrally acting force $F_\gamma$ maintains the droplet shape (FIG. 3C). The structure of SYBR Green I (SG) and its interaction with dsDNA are known. SG intercalates the DNA minor groove via its phenylquinilinium and benzothiazole aromatic systems, and the positively charged benzothiazole interacts electrostatically with the negatively charged phosphate groups of dsDNA. In addition, the dsDNA/SG complex is stabilized by the positively charged dimethylaminopropyl group, which extends along the minor groove for 3-4 base pairs. The overall size of the SG binding site is equal to 3.4 bp or 11.5 Å. Unbound SG is an amphiphilic molecule containing positively charged propyl groups as well as aromatic rings. Therefore, when SG intercalates dsDNA, the positively charged SG partially neutralizes the negatively charged phosphate backbone of dsDNA. When dsDNA is amplified, the dsDNA/SG complex is formed, which has high affinity for the oil-water interface. As the dsDNA/SG complex concentration increases, the interfacial tension decreases markedly (FIG. 6C).

The Role of the dsDNA/SG Complex in DOTS qPCR.

Figure 5B:
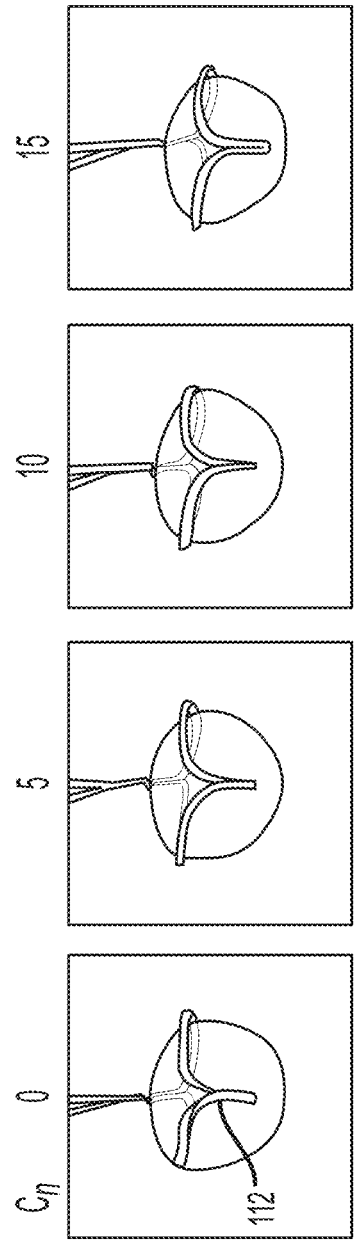
FIG. 5B is a series of digital images of the droplet-on-thermocouple submerged in oil. Images were taken every 5 thermal cycles and used to determine the droplet height.
Figure 7B:
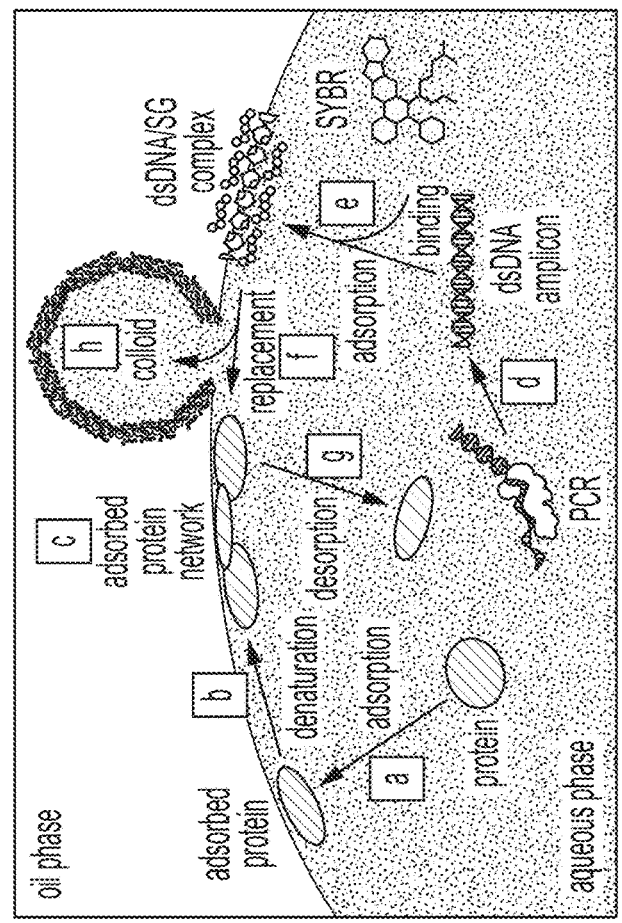
FIG. 7B is a molecular schematic illustrating adsorption at the oil-water interface: a) protein adsorption initially stabilizes the droplet; b) proteins undergo conformational change; c) proteins form networks; d) PCR produces dsDNA amplicons; e) SG intercalates dsDNA, forming relatively hydrophobic complexes; f,g) dsDNA/SG complexes replace the surface-bound proteins because of high interfacial affinity and high concentration (Vroman effect); h) adsorption of dsDNA/SG complexes decreases interfacial tension, and colloidal suspensions become energetically favorable. Femtoliter water droplets are emulsified in the oil phase, decreasing droplet-on-thermocouple volume.

Before PCR amplification, high-motility proteins with low interface affinity adsorb reversibly and are subsequently displaced by proteins that have high concentration, higher affinity for the interface, and lower motility; this is known as the Vroman effect. In DOT thermocycling, the dsDNA concentration is exponentially increased by PCR, and the relatively hydrophobic dsDNA/SG complex accumulates. Adsorption of the dsDNA/SG complex at the interface causes proteins to desorb, dramatically decreasing the interfacial tension. As the interfacial tension decreases, the entropy penalty of interaction between oil and water decreases as well (FIG. 7B). Since higher surface area to volume ratios are permitted when the surface energy is decreased, droplets with a volume of 0.5-4.2 fL separate from the droplet-on-thermocouple and become emulsified in the oil phase (FIG. 7A). As shown in FIGS. 5A and 5B, the decrease in interfacial tension, which leads to a decrease in the droplet-on-thermocouple volume, is dependent on $N_0$ of the reaction, because $N_t$ is reached at earlier cycles for reactions with higher $N_0$. There is a log-linear relationship between $N_0$ and the threshold cycle ($C_t$): $\log(N_0) = -0.48 C_t + 6.6$. This relationship can be used to quantify unknown $N_0$, in the range of $1.5 \times 10^2$ to $1.5 \times 10^5$ copies of bacterial genomic DNA. Typical clinical concentrations for IE range from $10^7$-$10^9$ CFU/g of vegetated heart valve tissue with inocula ranging from $10^4$-$10^9$ CFU (40). The quantitative range of DOTS qPCR is a good match for this clinical situation, considering the sample preparation method, sample size, and the limit of detection of $1.5 \times 10^2$ genomic copies.

Comparison of Interfacial Tension Detection with Fluorescence Detection.

Figure 6B:
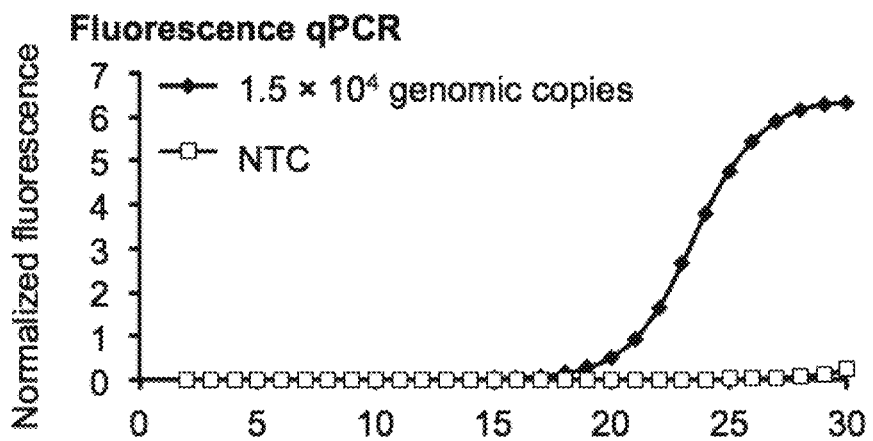
Figure 6C:
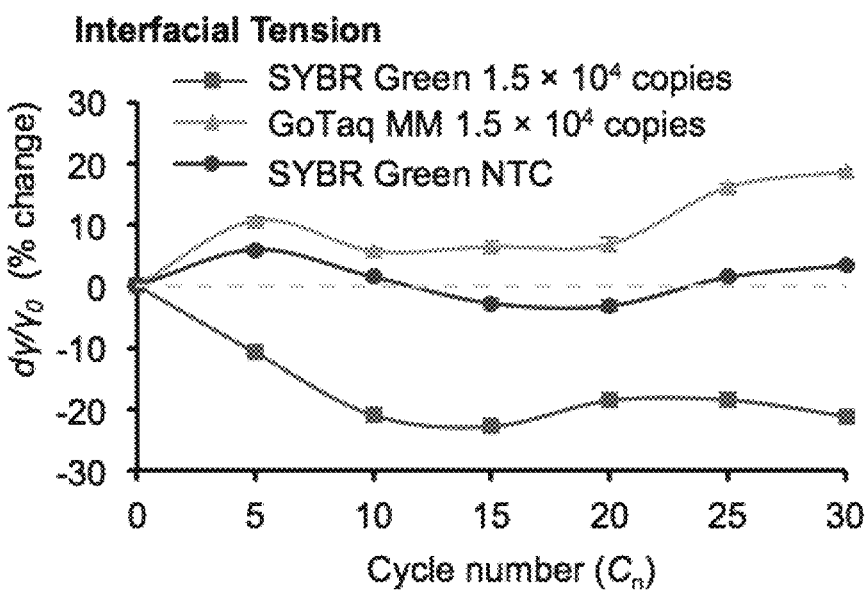
Figure 7A:
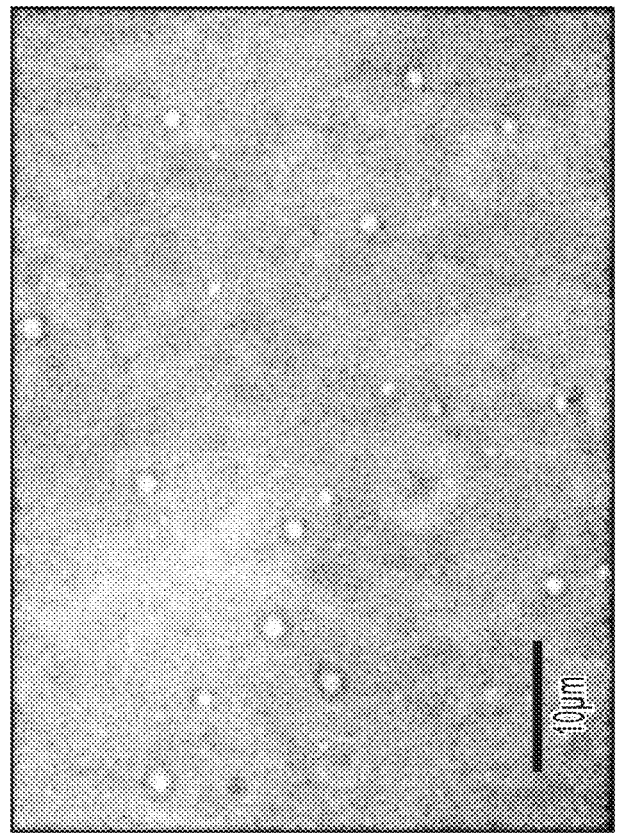
FIG. 7A is a bright-field microscope image showing water-in-oil droplets stabilized by dsDNA/SG complexes. The droplets ranged in diameter from 1-2 μm and in volume from 0.5-4.2 fL. These femtoliter droplets were observed in the oil phase following DNA amplification with SG.

FIGS. 6A-6C show that interfacial tension can be used to detect PCR amplification at earlier thermal cycles than can be achieved with fluorescence or gel electrophoresis. PCR amplification is described by Eq. 1, where E is the reaction efficiency, $C_n$ is the number of cycles, $N_0$ is the initial number of amplicons, and $N_n$ is the number of amplicons after n cycles.

$$N_n = N_0(E+1)^{C_n} \qquad \text{Equation (1)}$$

In the case of fluorescence detection, a threshold ($F_t$) can be chosen to calculate the corresponding threshold cycle ($C_t$). The number of amplicons at $C_t$ ($N_t$) is the same for any $N_0$. $N_t$ is used to compare the DOTS qPCR and fluorescence qPCR detection techniques. The standard curves for both the methods are presented in FIGS. 8A and 8B. For both the methods, $N_t$ is calculated from the intercept in the log-linear equation (Eq. 2) of the standard curve (48, 49).

$$\log N_0 = -C_t \log(E+1) + \log N_t \qquad \text{Equation (2)}$$

SG fluorescence is increased by 1000 times upon forming a complex with dsDNA, but this fluorescence signal is not detectable by fluorescence qPCR until $1.28 \times 10^{10}$ amplicons are present. In contrast, the detection threshold in DOTS qPCR is reached at $3.96 \times 10^6$ copies (FIG. 8A).

For interfacial tension detection, $N_t$ is assigned a physical meaning by using the Langmuir adsorption isotherm equation (Eq. 3), where θ is the fractional coverage (θ=Γ/$Γ_{max}$), Γ is the adsorbed amount, $Γ_{max}$ is the amount adsorbed at saturation, C is the equilibrium concentration, and $K_{ads}$ is the equilibrium constant for adsorption/desorption.

$$\theta = \frac{K_{ads}C}{1 + K_{ads}C} \qquad \text{Equation (3)}$$

The Langmuir adsorption isotherm equation describes the filling of available surface sites as a function of concentration. As the equilibrium concentration increases with each thermal cycle, a similar saturation effect is seen in the interfacial tension with respect to the cycle number (FIG. 6C). To apply this interfacial adsorption to interfacial tension, we must consider the energy associated with molecular adsorption. For this purpose, we turn to the Gibbs adsorption isotherm at constant temperature (Eq. 4), where γ is the interfacial tension, Γ is the adsorbed amount, and μ is the chemical potential.

$$d\gamma = -\Sigma \Gamma_i d\mu_i \qquad \text{Equation (4)}$$

From the Gibbs adsorption isotherm, it is shown that the interfacial tension (γ) is sensitive to the adsorbed amount (Γ) and the change in the interfacial tension (dγ) will be zero when $Γ_{max}$ is reached. The Langmuir and Gibbs adsorption isotherms allow us to define $N_t$ for DOTS qPCR as the amount of DNA amplicons necessary to cause a sufficiently large decrease in interfacial tension that results in a fractional volume loss of 4.8%.

Impact of DOTS qPCR on Medical Diagnostics and Biological Research.

The reduction in interfacial tension upon DNA amplification in the presence of SG causes a fractional loss of volume because femtoliter-sized water droplets become emulsified in the oil phase. Moreover, the logarithm of $N_0$ scales linearly with the fractional thermal cycle at which the percent decrease in droplet height reaches the 4.8% threshold. This relationship can be used for quantification in a manner identical to fluorescence qPCR but at a lower threshold cycle (FIGS. 8A and 8B). Quantification by DOTS qPCR can be accomplished in less than 4 thermal cycles and takes 2 minutes, 30 seconds (3 minutes 30 seconds including sample preparation/loading). Fluorescence qPCR systems require excitation and emission band-pass filters, a dichroic mirror, an expensive light source (tungsten-halogen lamp or argon ion laser), a sensitive detector (typically photomultiplier tube), a completely dark environment, and an external computer. In contrast, the DOTS qPCR detection system is composed of a single lens and a smartphone under ambient lighting. Furthermore, disposability is desired feature of medical diagnostics. All components of the DOTS qPCR device that come into contact with the sample—the semicircular channel, motor arm, thermocouple, heating element, and silicone oil—are inexpensive (less than \$20 for all components) and disposable.

PCR is widespread in biological research and medical diagnostics. While all users could benefit from the increased assay speed, the disclosed methodology could have an immediate impact on patients for whom time is truly of the essence. Therefore, DOTS qPCR can be used to diagnose tissue infection, which could result in informed clinical decision-making and a decreased loss of life. It is contemplated that the disclosed methodology could be used in the analysis of single cells, single nuclei, and single molecules. These applications require greater than 40 thermal cycles to reach the fluorescence detection threshold, and excessive thermocycling can decrease specificity by amplifying low-level background contamination and non-specific targets. Therefore, the low threshold cycle detection with the disclosed device and methods would improve the analysis of these small samples. The present disclosure is the first reported use of interfacial effects to detect PCR amplification. This is an important technical advancement, not only because of the simplicity of the thermocycler and detection apparatus, but also because it enables detection at low cycle numbers. Because of its extremely high speed, DOTS qPCR can be used unlike any existing technique for tissue infection diagnosis—in the clinic or operating room before initial prescription of therapy. With DOTS qPCR, infection diagnosis will be timely and surveillance of antibiotic resistance will be convenient and widespread.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An apparatus, comprising:
    two chambers containing a hydrophobic liquid, wherein a first chamber of the two chambers comprises a first heater maintaining the hydrophobic liquid at a first temperature, and a second chamber of the two chambers comprises a second heater maintaining the hydrophobic liquid at a second temperature;
    a channel hydraulically connecting the two chambers and containing the hydrophobic liquid, wherein a temperature gradient in the hydrophobic liquid between the first temperature and the second temperature is formed between the first chamber and the second chamber along the channel;
    a transparent window in the channel positioned between the two chambers;
    a movement device adapted to move between the two chambers and along the channel;
    a droplet manipulating device coupled to the movement device and immersed in the hydrophobic liquid, wherein the droplet manipulating device comprises a temperature sensing device comprising a looped thermocouple positioned inside a droplet within the droplet manipulating device; and
    a controller operably connected to the movement device and the temperature sensing device within the droplet manipulating device, the controller being configured to command the movement device along the channel based on a sensed temperature inside the droplet.

2. The apparatus of claim 1, further comprising a second temperature sensing device coupled to the movement device and configured to sense a temperature of the hydrophobic liquid.

3. The apparatus of claim 1, wherein the channel is arced.

4. The apparatus of claim 1, wherein the transparent window is positioned equidistant from the two chambers.

5. An apparatus, comprising:
a chamber containing a hydrophobic liquid and a heater maintaining the hydrophobic liquid at a temperature;
a channel hydraulically coupled to the chamber and extending from the chamber a distance sufficient to form a temperature gradient along the hydrophobic liquid;
a transparent window positioned on the channel;
a movement device adapted to move along the channel;
a droplet manipulating device coupled to the movement device and immersed in the hydrophobic liquid, wherein the droplet manipulating device comprises a temperature sensing device comprising a looped thermocouple positioned inside a droplet within the droplet manipulating device; and
a controller operably connected to the movement device and the temperature sensing device, the controller being configured to command the movement device along the channel based on a sensed temperature inside the droplet.

6. The apparatus of claim 5, further comprising a second temperature sensing device coupled to the movement device and configured to sense a temperature of the hydrophobic liquid.

7. The apparatus of claim 5, wherein the channel is arced.

8. The apparatus of claim 1, wherein the first temperature is 45-50° C. and the second temperature is 100-105° C., or wherein the first temperature is 100-105° C. and the second temperature is 45-50° C.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: oligonucleotide synthetic primer

<400> SEQUENCE: 1
tctgcaatag agatagccgc                                              20

<210> SEQ ID NO 2
<211> LENGTH: 20

```
<212> TYPE: DNA
<213> ORGANISM: Artificial Sequence
<220> FEATURE:
<223> OTHER INFORMATION: oligonucleotide synthetic primer

<400> SEQUENCE: 2
ggagtagcta tcccagcatt                                              20

<210> SEQ ID NO 3
<211> LENGTH: 20
<212> TYPE: DNA
<213> ORGANISM: Artificial Sequence
<220> FEATURE:
<223> OTHER INFORMATION: oligonucleotide synthetic primer

<400> SEQUENCE: 3
actcctacgg gaggcagcag                                              20

<210> SEQ ID NO 4
<211> LENGTH: 17
<212> TYPE: DNA
<213> ORGANISM: Artificial Sequence
<220> FEATURE:
<223> OTHER INFORMATION: oligonucleotide synthetic primer

<400> SEQUENCE: 4
attaccgcgg ctgctgg                                                 17

<210> SEQ ID NO 5
<211> LENGTH: 20
<212> TYPE: DNA
<213> ORGANISM: Artificial Sequence
<220> FEATURE:
<223> OTHER INFORMATION: oligonucleotide synthetic primer

<400> SEQUENCE: 5
agagtttgat cmtggctcag                                              20

<210> SEQ ID NO 6
<211> LENGTH: 17
<212> TYPE: DNA
<213> ORGANISM: Artificial Sequence
<220> FEATURE:
<223> OTHER INFORMATION: oligonucleotide synthetic primer

<400> SEQUENCE: 6
actgctgcct cccgtag                                                 17
```